US012564463B2

(12) United States Patent
Ho

(10) Patent No.: US 12,564,463 B2
(45) Date of Patent: Mar. 3, 2026

(54) ROBOTIC COLLISION BOUNDARY DETERMINATION

(71) Applicant: Auris Health, Inc., Santa Clara, CA (US)

(72) Inventor: Mingyen Ho, Santa Clara, CA (US)

(73) Assignee: Auris Health, Inc., Santa Clara, CA (US)

( * ) Notice: Subject to any disclaimer, the term of this patent is extended or adjusted under 35 U.S.C. 154(b) by 825 days.

(21) Appl. No.: 17/464,466

(22) Filed: Sep. 1, 2021

(65) Prior Publication Data

US 2022/0061941 A1 Mar. 3, 2022

Related U.S. Application Data

(63) Continuation of application No. PCT/IB2021/057962, filed on Aug. 31, 2021.

(60) Provisional application No. 63/073,860, filed on Sep. 2, 2020.

(51) Int. Cl.
*A61B 34/00* (2016.01)
*A61B 34/10* (2016.01)
*A61B 90/00* (2016.01)
*B25J 9/16* (2006.01)

(52) U.S. Cl.
CPC .............. *A61B 34/74* (2016.02); *A61B 34/10* (2016.02); *A61B 90/37* (2016.02); *B25J 9/1666* (2013.01); *B25J 9/1676* (2013.01); *A61B 2034/107* (2016.02)

(58) Field of Classification Search
CPC ... A61B 34/10; A61B 90/37; A61B 2034/107; A61B 34/74; B25J 9/1666; B25J 9/1676
See application file for complete search history.

(56) References Cited

U.S. PATENT DOCUMENTS

| | | | |
|---|---|---|---|
| 10,130,435 | B2 | 11/2018 | Mewes et al. |
| 10,464,209 | B2 | 11/2019 | Ho et al. |
| 11,280,690 | B2 | 3/2022 | Lin et al. |
| 11,701,783 | B2 | 7/2023 | Meyer et al. |
| 2008/0247506 | A1 | 10/2008 | Maschke |
| 2011/0224826 | A1 | 9/2011 | Maehara et al. |
| 2013/0325029 | A1 | 12/2013 | Hourtash et al. |

(Continued)

FOREIGN PATENT DOCUMENTS

| | | |
|---|---|---|
| CN | 105708461 A | 6/2016 |
| CN | 107205786 A | 9/2017 |

(Continued)

OTHER PUBLICATIONS

International Preliminary Report on Patentability for Appl. No. PCT/IB2021/057962, 4 pages.

(Continued)

*Primary Examiner* — Jay Khandpur

(74) *Attorney, Agent, or Firm* — Paradice & Li LLP

(57) ABSTRACT

Techniques relate to determining a region associated with an object to assist in controlling a robotic arm. For example, a system can determine that the robotic arm is positioned adjacent to an object within an environment. The system can determine a region in the environment that is associated with the object based at least in part on a position of a distal end of the robotic arm. The system can control the robotic arm or another robotic arm to move in the environment based at least in part on the region.

22 Claims, 11 Drawing Sheets

(56) References Cited

U.S. PATENT DOCUMENTS

| | | | |
|---|---|---|---|
| 2015/0251315 A1* | 9/2015 | Brandenberger .. | G05B 19/4061 |
| | | | 901/14 |
| 2017/0049517 A1 | 2/2017 | Felder et al. | |
| 2017/0143432 A1 | 5/2017 | Bowling et al. | |
| 2017/0252113 A1 | 9/2017 | Beelen et al. | |
| 2018/0036884 A1 | 2/2018 | Chen et al. | |
| 2019/0216411 A1 | 7/2019 | Henderson | |
| 2019/0299416 A1* | 10/2019 | Watanabe ................ | B25J 9/046 |
| 2020/0078097 A1 | 3/2020 | Gregerson et al. | |
| 2020/0171660 A1 | 6/2020 | Ho et al. | |
| 2020/0367977 A1* | 11/2020 | Liu ........................ | B25J 9/1676 |
| 2021/0059781 A1* | 3/2021 | Peine ..................... | A61B 34/37 |
| 2021/0077203 A1* | 3/2021 | Monteverde ........... | B25J 9/1633 |
| 2022/0378521 A1* | 12/2022 | Turgeman ................ | G06T 7/50 |
| 2023/0126611 A1* | 4/2023 | Itotani .................... | A61B 90/25 |
| | | | 606/130 |
| 2023/0165649 A1* | 6/2023 | Fitzsimons ............ | A61B 34/30 |
| | | | 700/245 |
| 2023/0172438 A1* | 6/2023 | Usui ....................... | A61B 34/25 |
| | | | 606/1 |

FOREIGN PATENT DOCUMENTS

| | | | | |
|---|---|---|---|---|
| CN | 111343942 A | | 6/2020 | |
| CN | 111417354 A | | 7/2020 | |
| CN | 117621039 A | * | 3/2024 | .............. B25J 18/00 |
| EP | 3628262 A1 | | 4/2020 | |
| JP | 2018-524186 A | | 8/2018 | |
| WO | 2013101273 A1 | | 7/2013 | |
| WO | 2016138124 A1 | | 9/2016 | |
| WO | 2016208140 A1 | | 12/2016 | |
| WO | 2017146890 A1 | | 8/2017 | |
| WO | 2018081136 A2 | | 5/2018 | |
| WO | 2019070482 A1 | | 4/2019 | |
| WO | 2019136039 A1 | | 7/2019 | |
| WO | 2020049464 A1 | | 3/2020 | |
| WO | WO-2021252425 A1 | * | 12/2021 | |

OTHER PUBLICATIONS

Search Report for appl No. PCT/IB2021/057962, dated Dec. 6, 2021, 3 pages.
Written Opinion for appl No. PCT/IB2021/057962, dated Dec. 6, 2021, 3 pages.
CN Office Action for Appl. No. 202180054122.7, dated Feb. 2, 2024, 10 pages.
China Second Office Action from Application No. 202180054122.7, dated Sep. 28, 2024, 6 pages.
Europe extended Search Report from Application No. 21863807.0, dated Sep. 11, 2024, 11 pages.
Office Action from Japan Patent Application No. 2023-514425, dated Feb. 18, 2025, 11 pages.
Decision on Rejection from China Patent Application No. 202180054122.7, dated Mar. 11, 2025, 19 pages.

* cited by examiner

SELECT THE BOUNDARY LINES OR COLLISION REGION
TO ADJUST THE COLLISION REGION

ROBOTIC COLLISION BOUNDARY DETERMINATION

RELATED APPLICATION(S)

This application is a continuation of International Application No. PCT/IB2021/057962, filed Aug. 31, 2021, and entitled ROBOTIC COLLISION BOUNDARY DETERMINATION, which claims the benefit of priority to U.S. Provisional Application No. 63/073,860, filed Sep. 2, 2020, and entitled ROBOTIC COLLISION BOUNDARY DETERMINATION, the disclosures of which are hereby incorporated by reference in their entirety.

BACKGROUND

Field

The present disclosure relates to the field of medical devices and procedures.

Description of Related Art

Various medical procedures involve the use of one or more medical instruments to investigate and/or treat patients. In some cases, multiple systems/devices are implemented to control a medical instrument to perform a procedure on a patient. The improper use of such systems, devices, and/or medical instruments can adversely affect the health of the patient and/or efficacy of the procedure.

SUMMARY

In some implementations, the present disclosure relates to a system comprising a robotic system including a first robotic arm configured to couple to a medical instrument, and control circuitry communicatively coupled to the robotic system. The control circuitry is configured to receive input data indicating that the first robotic arm is positioned adjacent to an object within an environment, determine a region in the environment that is associated with the object based at least in part on a position of a distal end of the first robotic arm, and control at least one of the first robotic arm or a second robotic arm of the robotic system to move in the environment without moving into the region.

In some embodiments, the first robotic arm may be configured to operate in an admittance control mode in which user manipulation of the first robotic arm moves the first robotic arm. The input data may be received upon the first robotic arm operating in the admittance control mode. Further, in some embodiments, the control circuitry may be configured to determine the region based at least in part on a position of the robotic system. The region may include the object and exclude the robotic system.

In some embodiments, the input data indicates that the first robotic arm is positioned adjacent to a first edge of the object. The control circuitry may be configured to receive additional input data indicating that the second robotic arm is positioned adjacent to a second edge of the object, and determine the region based at least in part on a position of a distal end of the second robotic arm. The control circuitry may be configured to determine the region by determining a first boundary of the region based at least in part on the position of the distal end of the first robotic arm and determining a second boundary of the region based at least in part on the position of the distal end of the second robotic arm.

In some embodiments, the input data indicates that the first robotic arm is positioned adjacent to a first edge of the object. The control circuitry may be configured to receive additional input data indicating that the first robotic arm is positioned adjacent to a second edge of the object, and determine the region based at least in part on a position of the distal end of the first robotic arm when the input data is received and a position of the distal end of the first robotic arm when the additional input data is received.

In some embodiments, the control circuitry is further configured to cause a visual representation of the region to be displayed, receive adjustment input data including an adjustment to the visual representation, and update the region based at least in part on the adjustment to the visual representation. Further, in some embodiments, the control circuitry is further configured to set the system to a procedure mode to perform a medical procedure, determine that at least one of the first robotic arm or the second robotic arm experienced a collision, and update the region based on at least one of a position the distal end of the first robotic arm or a position of the second robotic arm when the collision occurred.

In some implementations, the present disclosure relates to a method comprising enabling a first robotic arm to be moved manually, receiving, by control circuitry, input data indicating that the first robotic arm is positioned adjacent to one or more objects, determining, by the control circuitry, a collision region based at least in part on a position of an end of the first robotic arm, and based at least in part on the collision region, controlling, by the control circuitry, movement of at least one of the first robotic arm or a second robotic arm to perform a medical procedure.

In some embodiments, the input data indicates that the first robotic arm is positioned adjacent to a first edge of the one or more objects. The method may further comprise receiving additional input data indicating that the second robotic arm is positioned adjacent to a second edge of the one or more objects. The determining the collision region may further be based at least in part on a position of an end of the second robotic arm. The determining the collision region may comprise defining a first plane based at least in part on the position of the end of the first robotic arm, defining a second plane based at least in part on the position of the end of the second robotic arm, and determining the region based at least in part on the first plane, the second plane, and an intersection of the first plane with the second plane.

In some embodiments, the input data indicates that the first robotic arm is positioned adjacent to a first edge of the one or more objects. The method may further comprise receiving additional input data indicating that the first robotic arm is positioned adjacent to another edge of the one or more objects. The determining the collision region may comprise determining the collision region based at least in part on a position of the end of the first robotic arm when the input data is received and a position of the end of the first robotic arm when the additional input data is received. The determining the collision region may comprises defining a first plane based at least in part on the position of the end of the first robotic arm when the input data is received, defining a second plane based at least in part on the position of the end of the first robotic arm when the additional input data is received, and determining the region based at least in part on the first plane, the second plane, and an intersection of the first plane with the second plane.

In some embodiments, at least one of the first robotic arm or the second robotic arm is configured to connect to a medical instrument. The method may further comprise receiving, from an input device, input control data regarding movement of the medical instrument, and determining that the input control data is associated with movement of at least one of the first robotic arm or the second robotic arm into the collision region The controlling movement of at least one of the first robotic arm or the second robotic arm may comprise preventing movement of at least one of the first robotic arm or the second robotic arm into the collision region. The method may further comprise causing a notification to be displayed indicating that the input control data is associated with movement into the collision region, and receiving additional input data indicating whether or not to proceed into the collision region. The controlling movement of at least one of the first robotic arm or the second robotic arm may be based at least in part on the additional input data.

In some embodiments, the first robotic arm is connected to a robotic system. The receiving the input data and the controlling movement of at least one of the first robotic arm or the second robotic arm may occur while the robotic system is located at a same parked position. Further, in some embodiments, the end of the first robotic arm may be an end-effector end of the first robotic arm.

In some implementations, the present disclosure relates to a control system comprising a communication interface configured to communicate with a first robotic arm, and control circuitry communicatively coupled to the communication interface. The control circuitry may be configured to determine that the first robotic arm is positioned adjacent to a first edge of one or more objects within an environment, determine a collision region for the environment based at least in part on a position of a distal end of the first robotic arm, and control movement of at least one of the first robotic arm or a second robotic arm based at least in part on the collision region. At least one of the first robotic arm or the second robotic arm may be configured to couple to a medical instrument.

In some embodiments, the control circuitry may be further configured to receive, from an input device, input control data to control the medical instrument, and determine that the input control data is associated with movement of at least one of the first robotic arm or the second robotic arm into the collision region. The control circuitry may be configured to control movement of at least one of the first robotic arm or a second robotic arm by preventing movement of at least one of the first robotic arm or the second robotic arm into the collision area. Further, in some embodiments, the control circuitry is further configured to determine that the second robotic arm is positioned adjacent to a second edge of the one or more objects, and the control circuitry is configured to determine the collision region based at least in part on the position of the distal end of the first robotic arm and a position of a distal end of the second robotic arm.

In some embodiments, the control circuitry is further configured to determine that the first robotic arm is positioned adjacent to a second edge of the one or more objects. The control circuitry may be configured to determine the collision region based at least in part on the position of the distal end of the first robotic arm at the first edge of the one or more objects and a position of the distal end of the first robotic arm at the second edge of the one or more objects. Further, in some embodiments, the control circuitry is further configured to cause a visual representation of the collision region to be displayed, receive adjustment input data including an adjustment to the visual representation, and update the collision region based at least in part on the adjustment to the visual representation.

In some embodiments, the control circuitry is further configured to set the control system to a procedure mode to perform a medical procedure, determine that at least one of the first robotic arm or the second robotic arm experienced a collision, and update the collision region based on at least one of a position the distal end of the first robotic arm or a position of the second robotic arm when the collision occurred.

In some implementations, the present disclosure relates to one or more non-transitory computer-readable media storing computer-executable instructions that, when executed by control circuitry, cause the control circuitry to perform operations comprising determining that a first robotic arm is positioned adjacent to a first edge of one or more objects within an environment, determining a collision area for the environment based at least in part on a position of a distal end of the first robotic arm, and control movement of at least one of the first robotic arm or a second robotic arm based at least in part on the collision area. At least one of the first robotic arm or the second robotic arm may be configured to couple to a medical instrument.

In some embodiments, the operations further comprise determining that the second robotic arm is positioned adjacent to a second edge of the one or more objects. The determining the collision area may further be based at least in part on a position of a distal end of the second robotic arm. The determining the collision area may comprise defining a first plane based at least in part on the position of the distal end of the first robotic arm, defining a second plane based at least in part on the position of the distal end of the second robotic arm, and determining the collision area based at least in part on the first plane, the second plane, and an intersection of the first plane with the second plane.

In some embodiments, the operations further comprise determining that the first robotic arm is positioned adjacent to a second edge of the one or more objects. The determining the collision area may be based at least in part on the position of the distal end of the first robotic arm at the first edge of the one or more objects and a position of the distal end of the first robotic arm at the second edge of the one or more objects. The determining the collision area may comprise defining a first plane based at least in part on the position of the distal end of the first robotic arm at the first edge of the one or more objects, defining a second plane based at least in part on the position of the distal end of the first robotic arm at the second edge of the one or more objects, and determining the collision area based at least in part on the first plane, the second plane, and an intersection of the first plane with the second plane.

In some embodiments, the operations further comprise receiving, from an input device, input control data regarding movement of the medical instrument, determining that the input control data is associated with movement of at least one of the first robotic arm or the second robotic arm into the collision area. The controlling movement of at least one of the first robotic arm or the second robotic arm may comprise preventing movement of at least one of the first robotic arm or the second robotic arm into the collision area. Further, in some embodiments, the determining that the first robotic arm is positioned adjacent to the first edge of the one or more objects comprises receiving, upon the first robotic arm operating in an admittance control mode. The input data may indicate that the first robotic arm is positioned adjacent to the first edge of the one or more objects.

For purposes of summarizing the disclosure, certain aspects, advantages and features have been described. It is to be understood that not necessarily all such advantages may be achieved in accordance with any particular embodiment. Thus, the disclosed embodiments may be carried out in a manner that achieves or optimizes one advantage or group of advantages as taught herein without necessarily achieving other advantages as may be taught or suggested herein.

BRIEF DESCRIPTION OF THE DRAWINGS

Various embodiments are depicted in the accompanying drawings for illustrative purposes and should in no way be interpreted as limiting the scope of the disclosure. In addition, various features of different disclosed embodiments can be combined to form additional embodiments, which are part of this disclosure. Throughout the drawings, reference numbers may be reused to indicate correspondence between reference elements.

FIG. 5 illustrates a top view of a medical system as a physician moves a robotic system in accordance with one or more embodiments.

DETAILED DESCRIPTION

Figure 1:
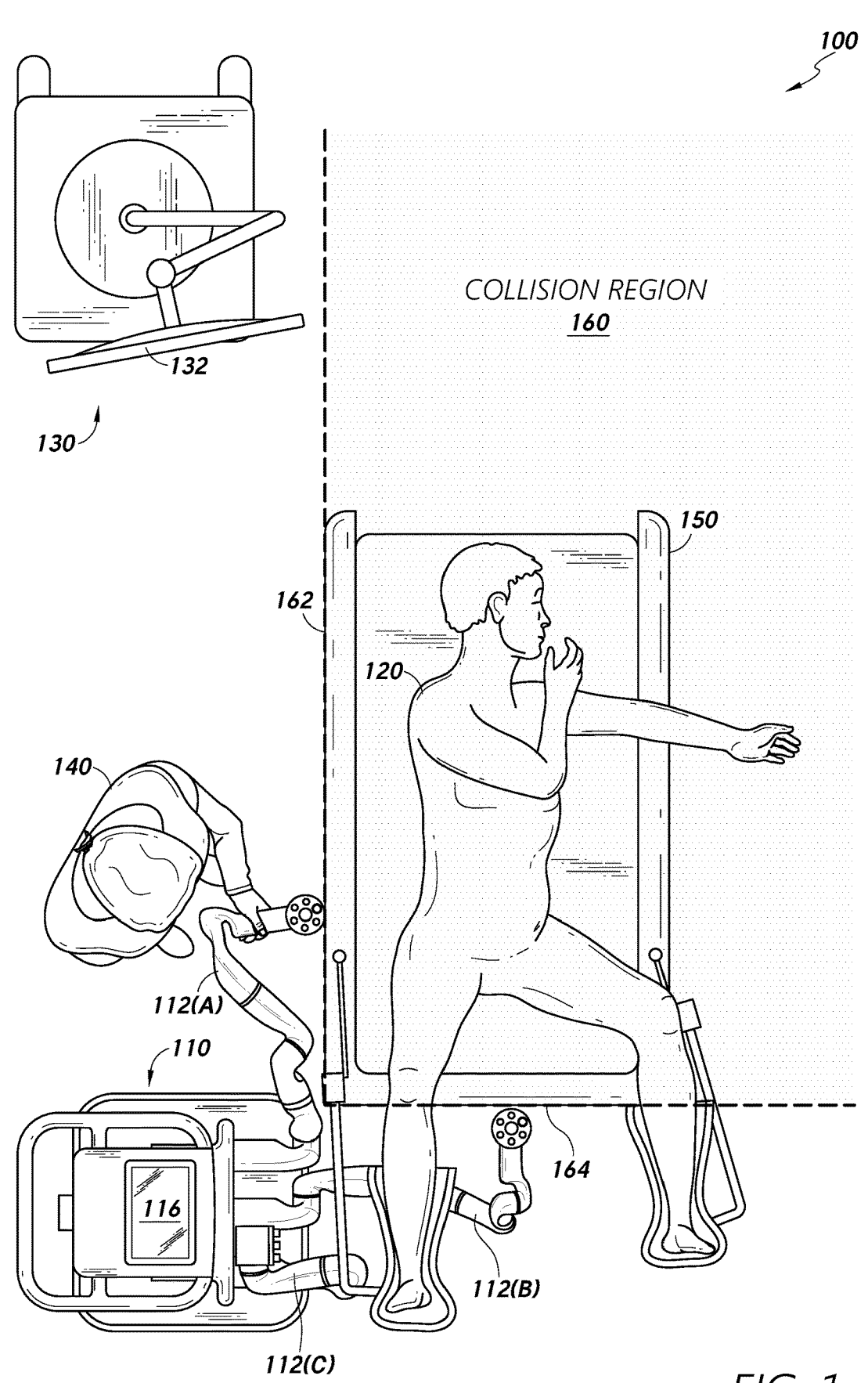
FIG. 1 illustrates an example medical system for performing various medical procedures in accordance with one or more embodiments.

The headings provided herein are for convenience only and do not necessarily affect the scope or meaning of the disclosure. Although certain embodiments and examples are disclosed below, subject matter extends beyond the specifically disclosed embodiments to other alternative embodiments and/or uses and to modifications and equivalents thereof. Thus, the scope of the claims that may arise here from is not limited by any of the particular embodiments described below. For example, in any method or process disclosed herein, the acts or operations of the method or process may be performed in any suitable sequence and are not necessarily limited to any particular disclosed sequence.

Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Certain standard anatomical terms of location can be used herein to refer to the anatomy of animals, and namely humans, with respect to the preferred embodiments. Although certain spatially relative terms, such as "outer," "inner," "upper," "lower," "below," "above," "vertical," "horizontal," "top," "bottom," and similar terms, are used herein to describe a spatial relationship of one device/element or anatomical structure to another device/element or anatomical structure, it is understood that these terms are used herein for ease of description to describe the positional relationship between element(s)/structures(s), as illustrated in the drawings. It should be understood that spatially relative terms are intended to encompass different orientations of the element(s)/structures(s), in use or operation, in addition to the orientations depicted in the drawings. For example, an element/structure described as "above" another element/structure may represent a position that is below or beside such other element/structure with respect to alternate orientations of the subject patient or element/structure, and vice-versa.

Overview

Medical procedures are often performed on patients in environments that include multiple objects, such as hospital beds, medical equipment, carts, surgical systems, and so on. In some implementations, robotic-assisted medical procedures can be performed in such environments, wherein robotic tools can enable a physician to perform endoscopic and/or percutaneous procedures. For example, the robotic tools can engage with and/or control one or more medical instruments to access a target site in a patient and/or perform a treatment at the target site. However, since the robotic tools may be unaware of the locations of objects within the environment, the robotic tools may be susceptible to collisions with the objects. For example, a robotic tool can collide with a hospital bed, patient on the hospital bed, medical equipment, and/or other objects in the environment while performing a medical procedure. This can cause harm to the patient and/or decrease the efficacy of the procedure.

The present disclosure relates to systems, devices, and methods for avoiding collisions with objects in an environment to assist in performing medical procedures. For example, a robotic system can include one or more robotic arms that are configured to couple to one or more medical instruments to perform a procedure. During configuration of the robotic system or at other times, the one or more robotic arms can be positioned adjacent to one or more objects within the environment. For example, a user can manually move the one or more robotic arms to contact one or more edges of the one or more objects. A collision region associated with the one or more objects can then be determined based on the position of the one or more robotic arms, such as the distal ends of the robotic arms. The one or more robotic arms and/or associated medical instruments can be controlled based on the collision region, such as by moving within the environment without traveling into the collision region, moving into the collision region upon confirmation by a user, and so on. By doing so, the robotic system can avoid collisions with objects in the environment/workspace (due to undesired movement of the robotic arms/medical instruments), which ultimately prevents harm to the patient, increases efficacy of the procedure, and so on.

Although certain aspects of the present disclosure are described herein in the context of renal, urological, and/or nephrological procedures, such as kidney stone removal/treatment procedures, it should be understood that such context is provided for convenience, and the concepts disclosed herein are applicable to any suitable medical procedure. For example, the following description is also applicable to other surgical/medical operations or medical procedures concerned with the removal of objects from a patient, including any object that can be removed from a treatment site or patient cavity (e.g., the esophagus, ureter, intestine, eye, etc.) via percutaneous and/or endoscopic access, such as, for example, gallbladder stone removal, lung (pulmonary/transthoracic) tumor biopsy, or cataract removal. However, as mentioned, description of the renal/urinary anatomy and associated medical issues and procedures is presented below to aid in the description of the concepts disclosed herein.

Example Medical System

FIG. 1 illustrates an example medical system 100 for performing various medical procedures in accordance with aspects of the present disclosure. The medical system 100 includes a robotic system 110 configured to engage with and/or control one or more medical instruments (not illustrated) to perform a procedure on a patient 120. The medical system 100 also includes a control system 130 configured to interface with the robotic system 110, provide information regarding the procedure, and/or perform a variety of other operations. For example, the control system 130 can include a display(s) 132 to present certain information to assist a physician 140. The medical system 100 can include a table 150 (e.g., bed) configured to hold the patient 120. Various acts are described herein as being performed by the physician 140. These acts can be performed directly by the physician 140, a user under the direction of the physician 140, another user (e.g., a technician), a combination thereof, and/or any other user.

The control system 130 can be coupled to the robotic system 110 and operate in cooperation with the robotic system 110 to perform a medical procedure on the patient 120. For example, the control system 130 can communicate with the robotic system 110 via a wireless or wired connection to control a medical instrument connected to the robotic system 110, receive an image(s) captured by a medical instrument (e.g., a scope), and so on. Additionally, or alternatively, the control system 130 can provide fluids to the robotic system 110 via one or more fluid channels, provide power to the robotic system 110 via one or more electrical connections, provide optics to the robotic system 110 via one or more optical fibers or other components, and so on. In some embodiments, the control system 130 can communicate with a medical instrument to receive sensor data (via the robotic system 110 and/or directly from the medical instrument). Sensor data can indicate or be used to determine a position and/or orientation of a medical instrument. Further, in some embodiments, the control system 130 can communicate with the table 150 to position the table 150 in a particular orientation or otherwise control the table 150. Moreover, in some embodiments, the control system 130 can communicate with an EM field generator (not illustrated) to control generation of an EM field around the patient 120.

The robotic system 110 can include one or more robotic arms 112 configured to engage with and/or control a medical instrument(s) to perform a procedure. For example, a distal end of the robotic arm 112 (e.g., end effector) can be physically connected to a medical instrument, which can be inserted and/or navigated within the patient to investigate and/or treat a target site. In the example of FIG. 1, the robotic arms 112 are illustrated without medical instruments attached. Although three robotic arms are illustrated, the robotic system 110 can include any number of robotic arms. Each robotic arm 112 can include multiple arm segments coupled to joints, which can provide multiple degrees of movement. The robotic system 110 can also be configured to couple to other types of instruments/devices, such as an electromagnetic (EM) field generator, which may be configured to generate an EM field that is detected by a sensor on a medical instrument. An EM field generator may be positioned near a treatment site during a phase of a procedure. The robotic system 110 can be arranged in a variety of ways depending on the particular procedure. In the examples of FIG. 1, the robotic system 110 also includes a display(s) 116 configured to display information and/or receive input.

The robotic system 110 can be coupled to any component of the medical system 100. In one example, the robotic system 110 is communicatively coupled to the control system 130 to receive a control signal from the control system 130 to perform an operation, such as to control a robotic arm 112 in a particular manner, manipulate a medical instrument, and so on. In another example, the robotic system 110 is configured to receive an image (also referred to as image data) from a scope depicting internal anatomy of the patient 120 and/or send the image to the control system 130, which can then be displayed on the display(s) 132. Furthermore, in some embodiments, the robotic system 110 is coupled to a component of the medical system 100, such as the control system 130, in such a manner as to allow for fluids, optics, power, or the like to be received therefrom.

In some embodiments, the robotic system 110 can be used to determine a region in an environment that is associated with an object (sometimes referred to as "a collision region" or "object zone"). For example, the robotic arm 112(A) can be moved to a left edge of the table 150 and the physician 140 can provide input indicating that the robotic arm 112(A) is positioned adjacent to an object in the environment, as shown in FIG. 1. The control system 130 and/or the robotic system 110 can then determine a position of a distal end of the robotic arm 112(A). In a similar fashion, the robotic arm 112(B) can be moved to a bottom edge of the table 150 and the physician 140 can provide input indicating that the robotic arm 112(B) is positioned adjacent to the object. The control system 130 and/or the robotic system 110 can then determine a position of a distal end of the robotic arm 112(B).

Based on the position of the distal end of the robotic arm 112(A) and/or the position of the distal end of the robotic arm 112(B), the control system 130 and/or the robotic system 110 can determine a collision region 160. For example, a first boundary 162 of the collision region 160 can be based on the position of the distal end of the robotic arm 112(A) and an intersection of the first boundary 162 with a second boundary 164. Further, the second boundary 164 can be based on the position of the distal end of the robotic arm 112(B) and the intersection of the first boundary 162 with the second boundary 164. The collision region 160 can include an area that excludes the robotic system 110 (e.g., the distal ends of the robotic arms 112(A) and 112(B)). For ease of illustration, the boundaries 162 and 164 are illustrated as extending to the edges of FIG. 1 from an intersection point of the boundaries 162 and 164. However, the boundaries 162 and 164 can be any length.

The robotic arms 112(A) and 112(B) can be positioned adjacent to the table 150 in a variety of manners. For example, the physician 140 can manually move the robotic arms 112(A) and 112(B), such as by selecting a button on a robotic arm to enable an admittance control mode associated with manual movement, as discussed in further detail below. Alternatively, or additionally, the physician 140 can use an I/O device associated with the control system 130/the robotic system 110 (e.g., a controller, mouse, etc.) to provide input that causes movement of the robotic arms 112(A) and 112(B). Although many examples are discussed in the context of positioning a first robotic arm, determining a position of the first robotic arm, and then positioning a second robotic arm and determining a position of the second robotic arm, the position of the first/second robotic arm can be determined at any time, such as after both arms have been positioned.

The control system 130 and/or the robotic system 110 can use the collision region 160 to control movement of the one or more robotic arms 112 and/or instruments coupled to the one or more robotic arms 112. By controlling movement of the one or more robotic arms 112 and/or instruments coupled to the one or more robotic arms 112 based on the collision region 160, collisions can be avoided with the table 150 and/or other objects within the collision region 160. The robotic arms 112 can generally operate in a robotically-controlled mode in which the robotic system 110 moves the robotic arms 112 without user manipulation of the robotic arms 112 or an admittance control mode in which a user manipulates the robotic arms 112 (e.g., manually moves the robotic arms 112). In either mode of operation, the robotic arms 112 can be controlled to move within the environment based on the collision region 160.

In some embodiments, the control system 130 and/or the robotic system 110 can move a robotic arm 112 into the collision region 160 based on override input from the physician 140. In one example, if the physician 140 provides input that would ordinarily move a robotic arm 112 into the collision region 160, the control system 130 can determine that the input would cause such movement into the collision region 160 and provide a notification/alert to the physician 140 (e.g., ask the physician 140 if he/she would like to override the configuration and move into the collision region 160). The notification/alert can indicate that the physician 140 is requesting movement that may potentially cause a collision with the robotic arm 112. The physician 140 can then confirm that he/she would like to continue with the movement into the collision region 160 (e.g., override avoidance of the collision region 160) or request that such movement not occur (e.g., avoid movement into the collision region 160). In another example, if the physician 140 attempts to manually move the robotic arm 112 into the collision region 160 (e.g., while operating in the admittance control mode), a similar notification/alert can be provided to the physician 140 and the robotic arm 112 can controlled based on a response from the physician 140.

Moreover, in some embodiments, the control system 130 and/or the robotic system 110 can control the robotic arms 112 to move within the environment without moving into the collision region 160. In one example, if the physician 140 provides input that would ordinarily move a robotic arm 112 into the collision region 160, the control system 130 can determine that the input would cause such movement into the collision region 160 and inhibit movement into the collision region 160. In another example, if the physician 140 attempts to manually move the robotic arm 112 into the collision region 160 (e.g., while operating in the admittance control mode), the robotic system 110 can prevent such movement, such as by stopping movement of the robotic arm 112 at a boundary of the collision region 160.

In some embodiments, the control system 130 and/or the robotic system 110 can control the robotic arms 112 to move within the collision region 160 (e.g., in either the robotically-controlled mode or admittance control mode) using a different algorithm than when moving outside the collision region 160. For example, the robotic arms 112 can be controlled to move slower in the collision region 160 than outside of the collision region 160, move with less force in the collision region 160 than outside the collision region 160, move into the collision region 160 as long as such movement is not within a predetermined distance to an initial location where a robotic arm was positioned to set the collision region 160, move within the collision region 160 with a different amount of resistance than movement outside the collision region 106 (e.g., when operating in the admittance control mode, cause the robotic arm 112 to feel heavier in the collision region 106 than outside the collision region 106), etc.

A collision region can represent an area/space within an environment in that includes an object, such as an area/space in which a collision may occur with a robotic arm/medical instrument. A boundary of a collision region can be represented/defined with a virtual surface/plane. Although many examples are discussed in the context of determining a collision region for a table, the techniques can be applied to other types of objects. For instance, the techniques can be used to determine a collision region for other medical equipment in the environment, a collision region for a patient, and so on. In some embodiments, multiple collision regions are determined for multiple objects in the environment, respectively. Moreover, although many collision regions are discussed as including two boundaries/surfaces, a collision region can include any number of boundaries/surfaces. For example, the collision region 160 for the table 150 can also include a boundary that is based on a height of the table 150, so that the robotic arms 112 can be permitted to move above the table 150.

In some embodiments, by enabling a user to manually position the robotic arms 112 adjacent to an object and determining a collision region based on the positions of the robotic arms 112, the techniques can intelligently/effectively determine the collision region without relying on other sensors/devices. For example, the techniques can avoid having to use additional components/sensors than those included in the medical system 100. Further, in some embodiments, the user is able to configure the collision region without providing input through a touchscreen, mouse, keyboard, or other types of input devices, which can be time-consuming and/or result in inaccurately defined collision regions.

A medical instrument can include a variety of types of instruments, such as a scope (sometimes referred to as an "endoscope"), a catheter, a needle, a guidewire, a litho-tripter, a basket retrieval device, forceps, a vacuum, a needle, a scalpel, an imaging probe, jaws, scissors, graspers, needle holder, micro dissector, staple applier, tacker, suction/irrigation tool, clip applier, and so on. A medical instrument can include a direct entry instrument, percutaneous entry instrument, and/or another type of instrument. In some embodiments, a medical instrument is a steerable device, while in other embodiments a medical instrument is a non-steerable device. In some embodiments, a surgical tool refers to a device that is configured to puncture or to be inserted through the human anatomy, such as a needle, a scalpel, a guidewire, and so on. However, a surgical tool can refer to other types of medical instruments.

The term "scope" or "endoscope" are used herein according to their broad and ordinary meanings and can refer to any type of elongate medical instrument having image generating, viewing, and/or capturing functionality and configured to be introduced into any type of organ, cavity, lumen, chamber, and/or space of a body. For example, a scope or endoscope can refer to a ureteroscope (e.g., for accessing the urinary tract), a laparoscope, a nephroscope (e.g., for accessing the kidneys), a bronchoscope (e.g., for accessing an airway, such as the bronchus), a colonoscope (e.g., for accessing the colon), an arthroscope (e.g., for accessing a joint), a cystoscope (e.g., for accessing the bladder), a borescope, and so on. A scope/endoscope, in some instances, may comprise a rigid or flexible tube, and may be dimensioned to be passed within an outer sheath, catheter, introducer, or other lumen-type device, or may be used without such devices. In some embodiments, a scope includes one or more working channels through which additional tools, such as lithotripters, basketing devices, forceps, etc., can be introduced into a treatment site.

The terms "direct entry" or "direct access" are used herein according to their broad and ordinary meaning and may refer to any entry of instrumentation through a natural or artificial opening in a patient's body. For example, a scope may be referred to as a direct access instrument, since the scope enters into the urinary tract of a patient via the urethra.

The terms "percutaneous entry" or "percutaneous access" are used herein according to their broad and ordinary meaning and may refer to entry, such as by puncture and/or minor incision, of instrumentation through the skin of a patient and any other body layers necessary to reach a target anatomical location associated with a procedure (e.g., the calyx network of the kidney). As such, a percutaneous access instrument may refer to a medical instrument, device, or assembly that is configured to puncture or to be inserted through skin and/or other tissue/anatomy, such as a needle, scalpel, guidewire, sheath, shaft, scope, catheter, and the like. However, it should be understood that a percutaneous access instrument can refer to other types of medical instruments in the context of the present disclosure. In some embodiments, a percutaneous access instrument refers to an instrument/device that is inserted or implemented with a device that facilitates a puncture and/or minor incision through the skin of a patient. For example, a catheter may be referred to as a percutaneous access instrument when the catheter is inserted through a sheath/shaft that has punctured the skin of a patient.

In some embodiments, a medical instrument includes a sensor (sometimes referred to as a position sensor) that is configured to generate sensor data. In examples, sensor data can indicate a position and/or orientation of the medical instrument and/or can be used to determine a position and/or orientation of the medical instrument. For instance, sensor data can indicate a position and/or orientation of a scope, which can include a roll of a distal end of the scope. A position and orientation of a medical instrument can be referred to as a pose of the medical instrument. A sensor can be positioned on a distal end of a medical instrument and/or any other location. In some embodiments, a sensor can provide sensor data to the control system 130, the robotic system 110, and/or another system/device to perform one or more localization techniques to determine/track a position and/or an orientation of a medical instrument.

In some embodiments, a sensor can include an electromagnetic (EM) sensor with a coil of conductive material. Here, an EM field generator can provide an EM field that is detected by the EM sensor on the medical instrument. The magnetic field can induce small currents in coils of the EM sensor, which can be analyzed to determine a distance and/or angle/orientation between the EM sensor and the EM field generator. Further, a sensor can include another type of sensor, such as a camera, a range sensor, a radar device, a shape sensing fiber, an accelerometer, a gyroscope, an accelerometer, a satellite-based positioning sensor (e.g., a global positioning system (GPS)), a radio-frequency transceiver, and so on.

In some embodiments, the medical system 100 can also include an imaging device (not illustrated in FIG. 1) which can be integrated into a C-arm and/or configured to provide imaging during a procedure, such as for a fluoroscopy-type procedure. The imaging device can be configured to capture/generate one or more images of the patient 120 during a procedure, such as one or more x-ray or CT images. In examples, images from the imaging device can be provided in real-time to view anatomy and/or medical instruments within the patient 120 to assist the physician 140 in performing a procedure. The imaging device can be used to perform a fluoroscopy (e.g., with a contrast dye within the patient 120) or another type of imaging technique.

The various components of the medical system 100 can be communicatively coupled to each other over a network, which can include a wireless and/or wired network. Example networks include one or more personal area networks (PANs), local area networks (LANs), wide area networks (WANs), Internet area networks (IANs), cellular networks, the Internet, etc. Further, in some embodiments, the components of the medical system 100 are connected for data communication, fluid/gas exchange, power exchange, and so on, via one or more support cables, tubes, or the like.

In some embodiments, the medical system 100 can be used to treat kidney stones. Kidney stone disease, also known as urolithiasis, is a medical condition that involves the formation in the urinary tract of a solid piece of material, referred to as "kidney stones," "urinary stones," "renal calculi," "renal lithiasis," or "nephrolithiasis." Urinary stones may be formed and/or found in the kidneys, the ureters, and the bladder (referred to as "bladder stones"). Such urinary stones can form as a result of mineral concentration in urinary fluid and can cause significant abdominal pain once such stones reach a size sufficient to impede urine flow through the ureter or urethra. Urinary stones may be formed from calcium, magnesium, ammonia, uric acid, cysteine, and/or other compounds or combinations thereof.

Generally, there are several methods for treating patients with kidney stones, including observation, medical treatments (such as expulsion therapy), non-invasive treatments (such as extracorporeal shock wave lithotripsy (ESWL)), and surgical treatments (such as ureteroscopy and percutaneous nephrolithotomy ("PCNL")). In surgical approaches (e.g., ureteroscopy and PCNL), the physician gains access to the pathology (i.e., the object to be removed; e.g., the stone), the stone is broken into smaller pieces or fragments, and the relatively small stone fragments/particulates are mechanically extracted from the kidney.

To remove urinary stones from the bladder and ureter, surgeons may insert a ureteroscope into the urinary tract through the urethra. Typically, a ureteroscope includes an endoscope at its distal end configured to enable visualization of the urinary tract. The ureteroscope can also include a lithotripsy device to capture or break apart urinary stones. During a ureteroscopy procedure, one physician/technician may control the position of the ureteroscope, while another other physician/technician may control the lithotripsy device (s). In order to remove relatively large stones from the kidneys (i.e., "kidney stones"), physicians may use a percutaneous nephrolithotomy ("PCNL") technique that involves inserting a nephroscope through the skin (i.e., percutaneously) and intervening tissue to provide access to the treatment site for breaking-up and/or removing the stone(s).

In several of the examples described herein, robotic-assisted percutaneous procedures can be implemented in connection with various medical procedures, such as kidney stone removal procedures, wherein robotic tools (e.g., one or more components of the medical system 100) can enable a physician/urologist to perform endoscopic (e.g., ureteroscopy) target access as well as percutaneous access/treatment. This disclosure, however, is not limited to kidney stone removal and/or robotic-assisted procedures. In some implementations, robotic medical solutions can provide relatively higher precision, superior control, and/or superior hand-eye coordination with respect to certain instruments compared to strictly manual procedures. For example, robotic-assisted percutaneous access to the kidney in accordance with some procedures can advantageously enable a urologist to perform both direct-entry endoscopic renal access and percutaneous renal access. Although some embodiments of the present disclosure are presented in the context of catheters, nephroscopes, ureteroscopes, and/or human renal anatomy, it should be understood that the principles disclosed herein may be implemented in any type of endoscopic/percutaneous procedure or another type of procedure.

In one illustrative procedure, the medical system 100 can be used to remove a kidney stone from the patient 120. During setup for the procedure, the physician 140 can use the robotic system 110 to determine the collision region 160 in the manner discussed herein. The one or more robotic arms 112 can then be arranged in various configurations/positions around the patient 120 to facilitate the procedure, such as stretched outwards to reach in between the legs of the patient 120 (e.g., align with the urethra of the patient 120), positioned near the abdomen of the patient 120, and so on. The physician 140 can connect a scope and/or other medical instrument to a robotic arm 112. The physician 140 can interact with the control system 130 (e.g., via an I/O device(s)) to cause the robotic system 110 to advance and/or navigate the scope from the urethra, through the bladder, up the ureter, and into the kidney where the stone is located. The control system 130 can provide information via the display(s) 132 regarding the scope to assist the physician 140 in navigating the scope, such as real-time images captured therewith. Once at the site of the kidney stone (e.g., within a calyx of the kidney), the scope can be used to designate/tag a target location for a catheter (which can be connected to another robotic arm 112) to access the kidney percutaneously. To minimize damage to the kidney and/or the surrounding anatomy, the physician 140 can designate a papilla as the target location for entering into the kidney percutaneously with the catheter. However, other target locations can be designated or determined.

The physician 140 can also interact with the control system 130 to cause the robotic system 110 to advance and/or navigate the catheter through a percutaneous access path to the target location designated by the scope. In some embodiments, a needle or another medical instrument is inserted into the patient 120 to create the percutaneous access path. The control system 130 can provide information via the display(s) 132 regarding the catheter to assist the physician 140 in navigating the catheter. For example, an interface(s) can provide image data from the perspective of the scope. The image data may depict the catheter (e.g., when within the field-of-view of an imaging device of the scope).

Once the scope and/or the catheter are located at the target location, the physician 140 can use the scope to break up the kidney stone and/or use the catheter to extract pieces of the kidney stone from the patient 120. For example, the scope can deploy a tool (e.g., a laser, a cutting instrument, etc.) to fragment the kidney stone into pieces and the catheter can suck out the pieces from the kidney through the percutaneous access path. In examples, the catheter and/or the scope can provide irrigation and/or aspiration to facilitate removal of the kidney stone. For instance, the catheter can be coupled to an irrigation and/or aspiration system.

During the procedure to remove the kidney stone, the control system 130 and/or the robotic system 110 can control the one or more robotic arms 112 based on the collision region 160. For example, if the physician 140 provides input that would ordinarily move a robotic arm 112 into the collision region 160, the control system 130 can determine that such input would cause the robotic arm 112 to move into the collision region 160 and provide a notification/alert to the physician 140 indicating that the input would cause movement into the collision region 160. The physician 140 can indicate whether or not to proceed with the movement.

The medical system 100 can provide a variety of benefits, such as providing guidance to assist a physician in performing a procedure (e.g., instrument tracking, instrument navigation, instrument calibration, etc.), enabling a physician to perform a procedure from an ergonomic position without the need for awkward arm motions and/or positions, enabling a single physician to perform a procedure with one or more medical instruments, avoiding radiation exposure (e.g., associated with fluoroscopy techniques), enabling a procedure to be performed in a single-operative setting, providing continuous suction to remove an object more efficiently (e.g., to remove a kidney stone), and so on. For example, the medical system 100 can provide guidance information to assist a physician in using various medical instruments to access a target anatomical feature while minimizing bleeding and/or damage to anatomy (e.g., critical organs, blood vessels, etc.). Further, the medical system 100 can provide non-radiation-based navigational and/or localization techniques to reduce physician and patient exposure to radiation and/or reduce the amount of equipment in the operating room. Moreover, the medical system 100 can provide functionality that is distributed between at least the control system 130 and the robotic system 110, which can be independently movable. Such distribution of functionality and/or mobility can enable the control system 130 and/or the robotic system 110 to be placed at locations that are optimal for a particular medical procedure, which can maximize working area around the patient and/or provide an optimized location for a physician to perform a procedure.

Although various techniques and systems are discussed as being implemented as robotically-assisted procedures (e.g., procedures that at least partly use the medical system 100), the techniques and systems can be implemented in other procedures, such as in fully-robotic medical procedures, human-only procedures (e.g., free of robotic systems), and so on. For example, the medical system 100 can be used to perform a procedure without a physician holding/manipulating a medical instrument and/or providing input to directly navigate the medical instrument (e.g., a fully-robotic procedure). That is, medical instruments that are used during a procedure can each be held/controlled by components of the medical system 100, such as the robotic arm(s) 112 of the robotic system 110.

Figure 2:
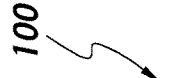
FIG. 2 illustrates a perspective view of the collision region and other aspects of the medical system of FIG. 1 in accordance with one or more embodiments.
Figure 2:
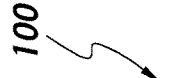

FIG. 2 illustrates a perspective view of the collision region 160 and other aspects of the medical system 100 of FIG. 1 in accordance with one or more embodiments. As shown, the collision region 160 includes the first boundary 162 associated with a first edge of the table 150 and the second boundary 164 associated with a second edge of the table 150 (e.g., the foot of the table 150). Here, the boundaries 162 and 164 each include/represent a substantially planar surface, which can extend any distance in an X, Y, and/or Z direction. In the example of FIGS. 1 and 2, the collision region 160 encompasses a three-dimensional (3D) space. That is, the collision region 160 is a 3D collision region. Here, the collision region 160 encompasses a space that includes the table 150 and a majority of the patient 120 (excluding a portion of the patient's 120 legs), while excluding a space that includes the robotic system 110. The control system 130 from FIG. 1 is not shown in FIG. 2. Although illustrated with a particular form (e.g., a 3D cubic-shaped region with planar surfaces), the collision region 160 can take other forms, such as a 2D collision region, nonplanar surfaces, other shapes, and so on. Further, although the robotic arms 112 are shown in various positions in the figures, it should be understood that such configurations are shown for convenience and illustrative purposes, and such robotic arms 112 can have different configurations.

In many illustrations herein, a collision region is defined for a table and a patient positioned on the table. For example, the control system 130 can establish the collision region 160 based on the physician 140 positioning the robotic arms 112 adjacent to the table 150, as discussed above, and an assumption that the patient 120 is positioned on the table 150. However, a collision region can be defined for any number of objects. In some instances, the physician 140 can provide input indicating a type of object associated with the collision region, such as a type of object that the robotic arms 112 are placed adjacent to. For example, the physician 140 can position one or more of the robotic arms 112 adjacent to the table 150 and provide input indicating that the one or more robotic arms 112 are positioned adjacent to the table 150. Then, the physician 140 can position one or more of the robotic arms 112 adjacent to the patient 120 (which can include positioning a robotic arm 112 adjacent to a portion of the patient's 120 leg that extends beyond the table 150) and provide input indicating that the type of object is a patient/user. The control system 130 can define separate collision regions for the table 150 and the patient 120 or determine a collision region that encompasses both the table 150 and the patient 120.

Example Control System and Robotic System

Figure 3:
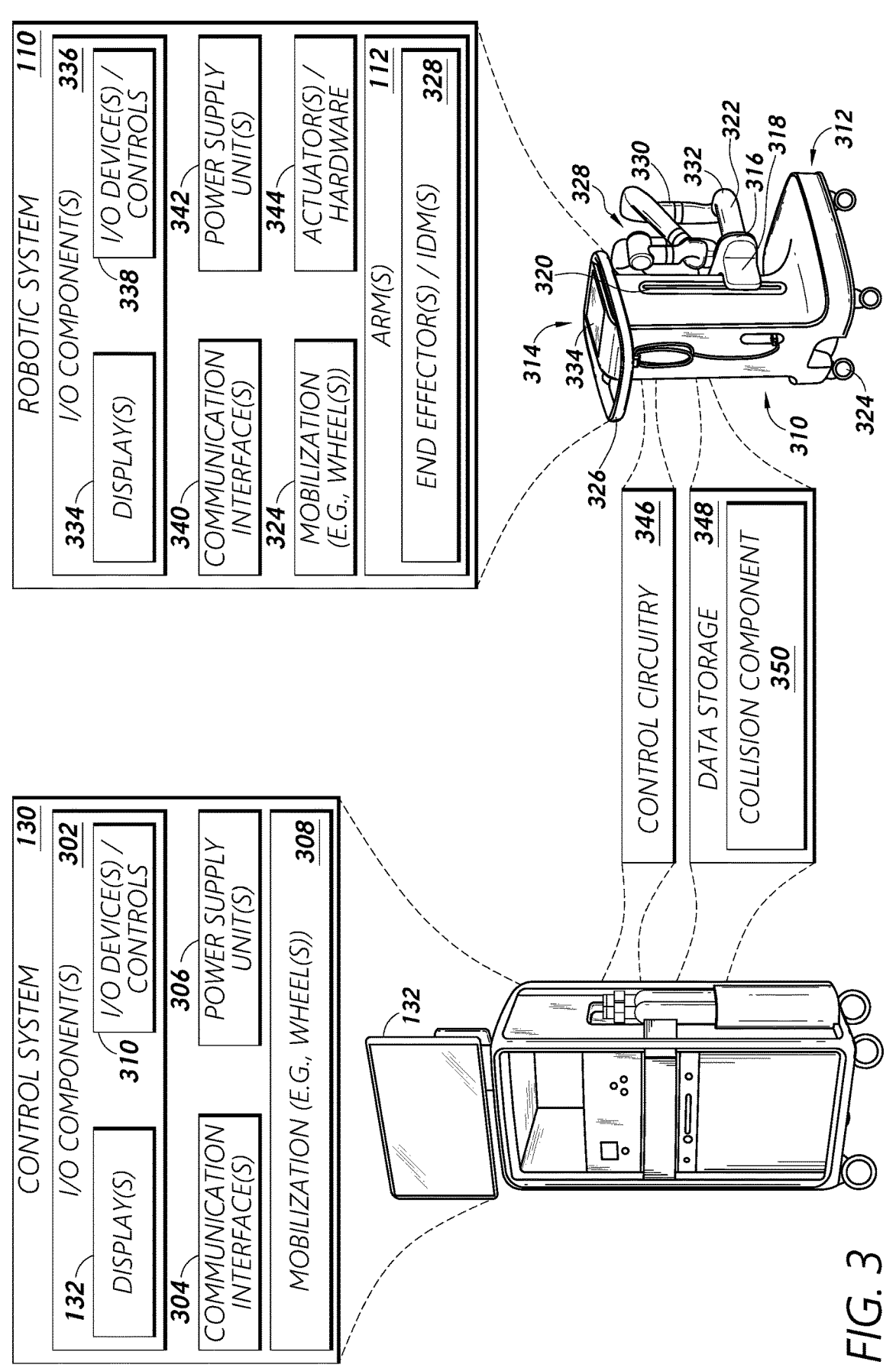
FIG. 3 illustrates example details of the control system and the robotic system of FIG. 1 in accordance with one or more embodiments.
Figure 4:
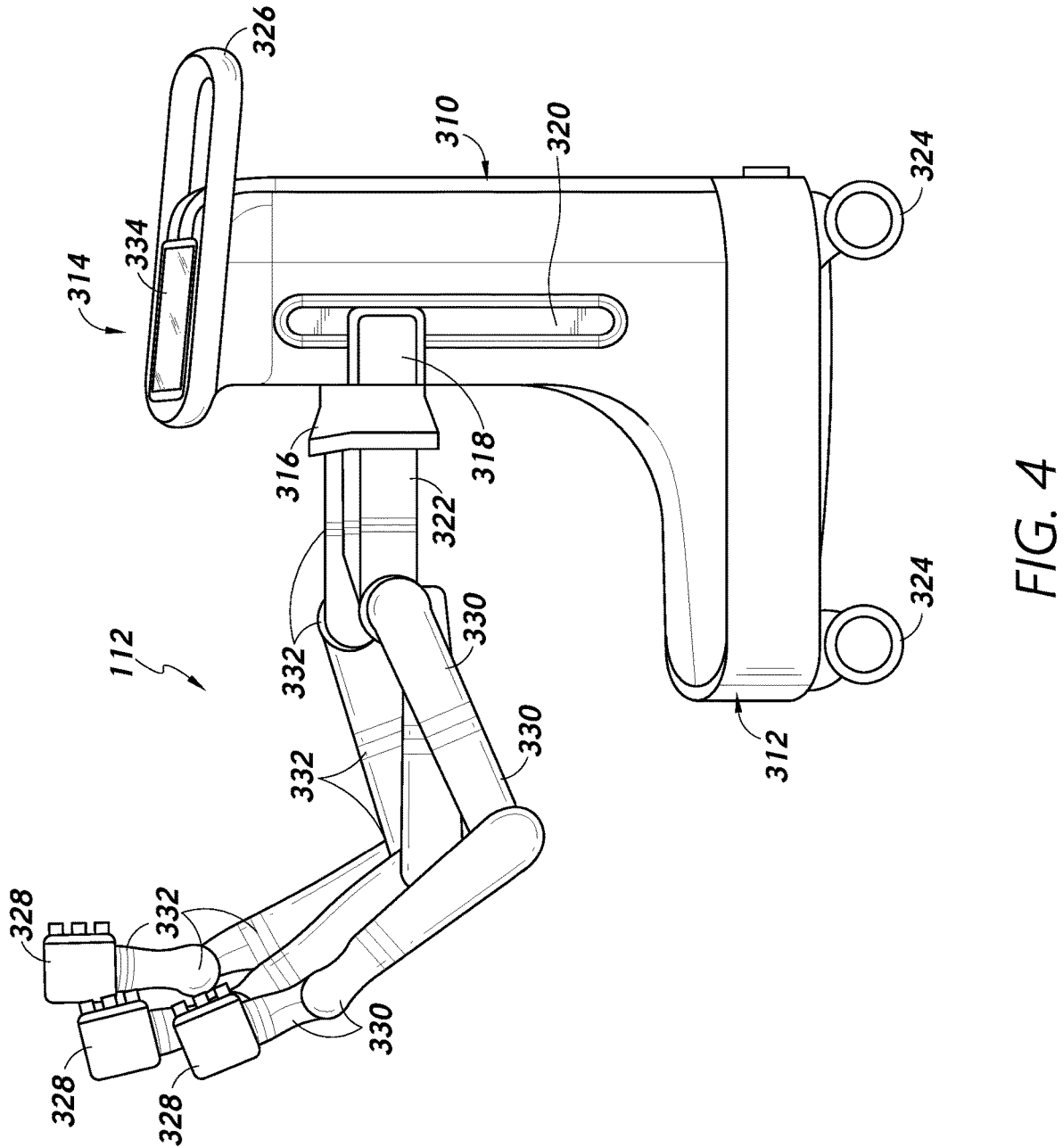
FIG. 4 illustrates example details of the robotic system of FIG. 1 in accordance with one or more embodiments.

FIG. 3 shows example details of the control system 130 and the robotic system 110 of FIG. 1, while FIG. 4 shows example details of the robotic system 110 in accordance with one or more embodiments. Although certain components of the control system 130 and/or the robotic system 110 are illustrated in FIGS. 3 and/or 4, it should be understood that additional components not shown can be included in embodiments in accordance with the present disclosure. Furthermore, any of the illustrated components can be omitted, interchanged, and/or integrated into other devices/systems, such as the table 150, a medical instrument, etc.

With reference to FIG. 3, the control system 130 can include one or more of the following components, devices, modules, and/or units (referred to herein as "components"), either separately/individually and/or in combination/collectively: one or more I/O components 302, one or more communication interfaces 304, one or more power supply units 306, and/or one or more mobilization components 308 (e.g., casters or other types of wheels). In some embodiments, the control system 130 can comprise a housing/enclosure configured and/or dimensioned to house or contain at least part of one or more of the components of the control system 130. In this example, the control system 130 is illustrated as a cart-based system that is movable with the one or more mobilization components 308. In some cases, after reaching the appropriate position, the one or more mobilization components 308 can be immobilized using wheel locks to hold the control system 130 in place. However, the control system 130 can be implemented as a stationary system, integrated into another system/device, and so on.

The various components of the control system 130 can be electrically and/or communicatively coupled using certain connectivity circuitry/devices/features, which can or may not be part of control circuitry. For example, the connectivity feature(s) can include one or more printed circuit boards configured to facilitate mounting and/or interconnectivity of at least some of the various components/circuitry of the control system 130. In some embodiments, two or more of the components of the control system 130 can be electrically and/or communicatively coupled to each other.

The one or more I/O components/devices 302 can include a variety of components to receive input and/or provide output, such as to interface with a user to assist in performing a medical procedure. The one or more I/O components 302 can be configured to receive touch, speech, gesture, or any other type of input. In examples, the one or more I/O components 302 can be used to provide input regarding control of a device/system, such as to control the robotic system 110, navigate a scope or other medical instrument attached to the robotic system 110, control the table 150, control a fluoroscopy device, and so on. For example, the physician 140 can provide input via the I/O component(s) 302 and, in response, the control system 130 can send control signals to the robotic system 110 to manipulate a medical instrument. In examples, the physician 140 can use the same I/O device to control multiple medical instruments (e.g., switch control between the instruments).

As shown, the one or more I/O components 302 can include the one or more displays 132 (sometimes referred to as "the one or more display devices 132") configured to display data. The one or more displays 132 can include one or more liquid-crystal displays (LCD), light-emitting diode (LED) displays, organic LED displays, plasma displays, electronic paper displays, and/or any other type(s) of technology. In some embodiments, the one or more displays 132 include one or more touchscreens configured to receive input and/or display data. Further, the one or more I/O components 302 can include one or more I/O devices/controls 310, which can include a touch pad, controller (e.g., hand-held controller, video-game-type controller, etc.), mouse, keyboard, wearable device (e.g., optical head-mounted display), virtual or augmented reality device (e.g., head-mounted display), etc. Additionally, the one or more I/O components 302 can include one or more speakers configured to output sounds based on audio signals and/or one or more microphones configured to receive sounds and generate audio signals. In some embodiments, the one or more I/O components 302 include or are implemented as a console.

In some embodiments, the one or more I/O components 302 can output information related to a procedure. For example, the control system 130 can receive real-time images that are captured by a scope and display the real-time images and/or visual representations of the real-time images via the display(s) 132. The display(s) 132 can present an interface(s), such as any of the interfaces discussed herein, which can include image data from the scope and/or another medical instrument. Additionally, or alternatively, the control system 130 can receive signals (e.g., analog, digital, electrical, acoustic/sonic, pneumatic, tactile, hydraulic, etc.) from a medical monitor and/or a sensor associated with a patient, and the display(s) 132 can present information regarding the health or environment of the patient. Such information can include information that is displayed via a medical monitor including, for example, a heart rate (e.g., ECG, HRV, etc.), blood pressure/rate, muscle bio-signals (e.g., EMG), body temperature, blood oxygen saturation (e.g., $SpO_2$), $CO_2$, brainwaves (e.g., EEG), environmental and/or local or core body temperature, and so on.

The one or more communication interfaces 304 can be configured to communicate with one or more device/sensors/systems. For example, the one or more communication interfaces 304 can send/receive data in a wireless and/or wired manner over a network. A network in accordance with embodiments of the present disclosure can include a local area network (LAN), wide area network (WAN) (e.g., the Internet), personal area network (PAN), body area network (BAN), etc. In some embodiments, the one or more communication interfaces 304 can implement a wireless technology, such as Bluetooth, Wi-Fi, near field communication (NFC), or the like.

The one or more power supply units 306 can be configured to manage and/or provide power for the control system 130 (and/or the robotic system 110, in some cases). In some embodiments, the one or more power supply units 306 include one or more batteries, such as a lithium-based battery, a lead-acid battery, an alkaline battery, and/or another type of battery. That is, the one or more power supply units 306 can comprise one or more devices and/or circuitry configured to provide a source of power and/or provide power management functionality. Moreover, in some embodiments the one or more power supply units 306 include a mains power connector that is configured to couple to an alternating current (AC) or direct current (DC) mains power source.

Although not shown in FIG. 3, the control system 130 can include and/or control other components, such as one or more pumps, flow meters, valve controls, and/or fluid access components in order to provide controlled irrigation and/or aspiration capabilities to a medical instrument (e.g., a scope), a device that can be deployed through a medical instrument, and so on. In some embodiments, irrigation and aspiration capabilities can be delivered directly to a medical instrument through separate cable(s). Further, the control system 130 can include a voltage and/or surge protector designed to provide filtered and/or protected electrical power to another device, such as the robotic system 110, thereby avoiding placement of a power transformer and other auxiliary power components in robotic system 110, resulting in a smaller, more moveable robotic system 110.

In some embodiments, the control system 130 can include support equipment for sensors deployed throughout the medical system 100. For example, the control system 130 can include opto-electronics equipment for detecting, receiving, and/or processing data received from optical sensors and/or cameras. Such opto-electronics equipment can be used to generate real-time images for display in any number of devices/systems, including in the control system 130. Similarly, the control system 130 can include an electronic subsystem for receiving and/or processing signals received from deployed electromagnetic (EM) sensors. In some embodiments, the control system 130 can also be used to house and/or position an EM field generator for detection by EM sensors in or on a medical instrument.

Further, in some embodiments, the control system 130 can be coupled to the robotic system 110, the table 150, and/or a medical instrument, through one or more cables or connections (not shown). In some implementations, support functionality from the control system 130 can be provided through a single cable, simplifying and de-cluttering an operating room. In other implementations, specific functionality can be coupled in separate cabling and connections. For example, while power can be provided through a single power cable, the support for controls, optics, fluidics, and/or navigation can be provided through a separate cable.

With reference to FIGS. 3 and 4, the robotic system 110 generally includes an elongated support structure 310 (also referred to as a "column"), a robotic system base 312, and a console 314 at the top of the column 310. The column 310 can include one or more carriages 316 (also referred to as "the arm support 316") for supporting the deployment of one or more the robotic arms 112. The carriage 316 can include individually configurable arm mounts that rotate along a perpendicular axis to adjust the base of the robotic arms 112 for positioning relative to a patient. The carriage 316 also includes a carriage interface 318 that allows the carriage 316 to vertically translate along the column 310. The carriage interface 318 can be connected to the column 310 through slots, such as slot 320, that are positioned on opposite sides of the column 310 to guide the vertical translation of the carriage 316. The slot 320 can include a vertical translation interface to position and/or hold the carriage 316 at various vertical heights relative to the base 312. Vertical translation of the carriage 316 allows the robotic system 110 to adjust the reach of the robotic arms 112 to meet a variety of table heights, patient sizes, physician preferences. etc. Similarly, the individually configurable arm mounts on the carriage 316 allow a robotic arm base 322 of the robotic arms 112 to be angled in a variety of configurations. The column 310 can internally comprise mechanisms, such as gears and/or motors, that are designed to use a vertically aligned lead screw to translate the carriage 316 in a mechanized fashion in response to control signals generated in response to user inputs, such as inputs from an I/O device(s).

The base 312 can balance the weight of the column 310, the carriage 316, and/or robotic arms 112 over a surface, such as the floor. Accordingly, the base 312 can house heavier components, such as one or more electronics, motors, power supply, etc., as well as components that enable movement and/or immobilize the robotic system 110. For example, the base 312 can include rollable wheels 324 (also referred to as "the casters 324" or "the mobilization components 324") that allow for the robotic system 110 to move around the room for a procedure. After reaching an appropriate position, the casters 324 can be immobilized using wheel locks to hold the robotic system 110 in place during the procedure. As shown, the robotic system 110 also includes a handle 326 to assist with maneuvering and/or stabilizing the robotic system 110. In this example, the robotic system 110 is illustrated as a cart-based robotically-enabled system that is movable. However, the robotic system 110 can be implemented as a stationary system, integrated into a table, and so on.

The robotic arms 112 can generally comprise robotic the arm bases 322 and end effectors 328, separated by a series of linkages 330 that are connected by a series of joints 332. Each joint 332 can comprise an independent actuator and each actuator can comprise an independently controllable motor. Each independently controllable joint 332 represents an independent degree of freedom available to the robotic arm 112. For example, each of the arms 112 can have seven joints, and thus, provide seven degrees of freedom. However, any number of joints can be implemented with any degrees of freedom. In examples, a multitude of joints can result in a multitude of degrees of freedom, allowing for "redundant" degrees of freedom. Redundant degrees of freedom allow the robotic arms 112 to position their respective end effectors 328 at a specific position, orientation, and/or trajectory in space using different linkage positions and/or joint angles. In some embodiments, the end effectors 328 can be configured to engage with and/or control a medical instrument, a device, an object, and so on. The freedom of movement of the arms 112 can allow the robotic system 110 to position and/or direct a medical instrument from a desired point in space and/or allow a physician to move the arms 112 into a clinically advantageous position away from the patient to create access, while avoiding arm collisions.

The end effector 328 of each of the robotic arms 112 may comprise an instrument device manipulator (IDM), which may be attached using a mechanism changer interface (MCI). In some embodiments, the IDM can be removed and replaced with a different type of IDM, for example, a first type of IDM can manipulate an endoscope, while a second type of IDM can manipulate a catheter. Another type of IDM may be configured to hold an electromagnetic field generator. An MCI can include connectors to transfer pneumatic pressure, electrical power, electrical signals, and/or optical signals from the robotic arm 112 to the IDM. The IDMs 328 may be configured to manipulate medical instruments (e.g., surgical tools/instruments) using techniques including, for example, direct drives, harmonic drives, geared drives, belts and pulleys, magnetic drives, and the like. In some embodiments, the IDMs 328 can be attached to respective ones of the robotic arms 112, wherein the robotic arms 112 are configured to insert or retract the respective coupled medical instruments into or out of the treatment site.

In some embodiments, the robotic arms 112 can be configured to control a position, orientation, and/or tip articulation of a medical instrument (e.g., a sheath and/or a leader of a scope). For example, the robotic arms 112 can be configured/configurable to manipulate the scope using elongate movement members. The elongate movement members can include one or more pull wires (e.g., pull or push wires), cables, fibers, and/or flexible shafts. To illustrate, the robotic arms 112 can be configured to actuate multiple pull wires coupled to the scope to deflect the tip of the scope. Pull wires can include any suitable or desirable materials, such as metallic and/or non-metallic materials such as stainless steel, Kevlar, tungsten, carbon fiber, and the like. In some embodiments, the scope is configured to exhibit nonlinear behavior in response to forces applied by the elongate movement members. The nonlinear behavior can be based on stiffness and compressibility of the scope, as well as variability in slack or stiffness between different elongate movement members.

As shown, the console 314 is positioned at the upper end of column 310 of the robotic system 110. The console 314 can include a display(s) 334 to provide a user interface for receiving user input and/or providing output (e.g., a dual-purpose device, such as a touchscreen) to provide a physician/user with pre-operative and/or intra-operative data. Potential pre-operative data on the console/display 334 can include pre-operative plans, navigation and mapping data derived from pre-operative computerized tomography (CT) scans, and/or notes from pre-operative patient interviews. Intra-operative data can include optical information provided from the tool, sensor and coordinate information from sensors, as well as vital patient statistics, such as respiration, heart rate, and/or pulse. The console 314 can be positioned and tilted to allow a physician to access the console 314 from the side of the column 314 opposite arm support 316. From this position, the physician may view the console 314, robotic arms 112, and patient while operating the console 314 from behind the robotic system 110.

The robotic system 110 can include one or more I/O components/devices 336 to receive input and/or provide output, such as to interface with a user. The one or more I/O components 336 can be configured to receive touch, speech, gesture, or any other type of input. In examples, the one or more I/O components 336 can be used to provide input regarding control of a device/system, such as to control/configure the robotic system 110. As shown, the one or more I/O components 334 can include the one or more displays 334 configured to display data. The one or more displays 334 can include one or more liquid-crystal displays (LCD), light-emitting diode (LED) displays, organic LED displays, plasma displays, electronic paper displays, and/or any other type(s) of technology. In some embodiments, the one or more displays 334 include one or more touchscreens configured to receive input and/or display data. Further, the one or more I/O components 336 can include one or more I/O devices/controls 338, which can include a touch pad, controller, mouse, keyboard, wearable device (e.g., optical head-mounted display), virtual or augmented reality device (e.g., head-mounted display), etc. Additionally, the one or more I/O components 336 can include one or more speakers configured to output sounds based on audio signals and/or one or more microphones configured to receive sounds and generate audio signals. In some embodiments, the one or more I/O components 336 include or are implemented as the console 314. Further, the one or more I/O components 336 can include one or more buttons that can be physically pressed, such as a button on a distal end of a robotic arm (which can enable an admittance control mode), as illustrated in further detail in reference to FIG. 6.

The various components of the robotic system 110 can be electrically and/or communicatively coupled using certain connectivity circuitry/devices/features, which can or may not be part of control circuitry. For example, the connectivity feature(s) can include one or more printed circuit boards configured to facilitate mounting and/or interconnectivity of at least some of the various components/circuitry of the robotic system 110. In some embodiments, two or more of the components of the robotic system 110 can be electrically and/or communicatively coupled to each other.

In some embodiments, one or more of the robotic arms 112 and/or the robotic system 110 can be configured to operate an admittance control mode. As used herein, the term "admittance control mode" (or simply "admittance mode") can refer to a control mode of a robotic arm 112/robotic system 110 in which the user controls the movement of the robotic arm 112 by applying forces thereto. For example, when operating in the admittance control mode, a robotic arm 112 can be manually moved by a user without using electronic user controls, such as by grasping the robotic arm 112 and applying a force thereto. As such, the user may be able to directly control the position of the robotic arm. The robotic arm 112 can include a driving component(s) configured to reposition and/or maintain the current pose (e.g., orientation and position) of the robotic arm 112 (e.g., motor/actuator to control movement of the robotic arm 112). Thus, in order to provide admittance control functionality, the robotic system 110/control system 130 can measure the force imparted to the robotic arm 112 by the user and actuate one or more of the driving components using the measured force as an input value.

To illustrate, when the admittance control mode is enabled, the robotic arm 112 can be freely moved by the user with manual manipulation of the robotic arm 112 based on a force applied to the robotic arm. For example, the user can grab the distal end of the robotic arm 112 and apply a force to position the distal end of the robotic arm 112 (and/or other portions of the robotic arm 112) at a desired position. When the admittance control mode is disabled and/or a force applied to the robotic arm 112 is less than a threshold, the robotic arm 112 can remain fixed to a position (e.g., inhibit manual movement of the robotic arm 112). In some cases of the admittance control mode, such as when positioning a robotic arm 112 at boundary to determine a collision region, the robotic arm 112 can be moved in a X, Y, Z manner without changing an orientation of an end effector of the robotic arm 112 (e.g., a user cannot tilt the robotic arm 112). However, in other embodiments, the orientation of the robotic arm 112 can be changed in the admittance control mode. Thus, the robotic system 110 can be configured to receive user input in the form of forces applied directly to a robotic arm 112 by the user, while in an admittance control mode.

The robotic arms 112/robotic system 110 can enter/exit the admittance control mode in a variety of manners. For example, a user can provide input via the robotic system 110/control system 130 (e.g., an interface, controller, etc.), provide input via a button on a robotic arm 112, or otherwise provide input to enable/disable an admittance control mode. Although the admittance control mode is discussed in many examples as being enabled/disabled in the context of pressing the button on a robotic arm 112, the admittance control mode can be enabled/disabled in a variety of manners, such as through any type of I/O device.

The robotic arms 112 can generally exhibit some amount of resistance when operating in the admittance control mode. The amount of resistance can affect the amount of force needed to move the robotic arm 112, to move the robotic arm 112 at a particular speed, to move the robotic arm 112 a particular distance, etc. As such, an amount of resistance associated with manual movement of a robotic arm 112 can be indicative of a force exerted back to the user (e.g., felt by the user) when manually moving the robotic arm 112. In some embodiments, one or more actuators/ hardware of a robotic arm 112 can be controlled to configure an amount of resistance for manual movement of the robotic arm 112. For example, a motor in a joint of a robotic arm 112 can be controlled based on a resistance parameter/value such that the robotic arm 112 exhibits a particular amount of resistance when the robotic arm 112 is moved by a user. In some embodiments, when operating in the admittance control mode, one or more parameters can be used to determine a speed to move the robotic arm 112, such as a force applied by a user on the robotic arm 112, virtual mass of the robotic arm 112, and/or virtual damping. The virtual mass can indicate how heavy the robotic arm 112 feels by the user (e.g., acceleration of robot motion), while virtual damping can provide a resistance feel to the user (e.g., how fast the robotic arm 112 moves).

The one or more communication interfaces 340 can be configured to communicate with one or more device/sensors/systems. For example, the one or more communication interfaces 340 can send/receive data in a wireless and/or wired manner over a network. A network in accordance with embodiments of the present disclosure can include a local area network (LAN), wide area network (WAN) (e.g., the Internet), personal area network (PAN), body area network (BAN), etc. In some embodiments, the one or more communication interfaces 340 can implement a wireless technology such as Bluetooth, Wi-Fi, near field communication (NFC), or the like.

The one or more power supply units 342 can be configured to manage and/or provide power for the robotic system 110. In some embodiments, the one or more power supply units 342 include one or more batteries, such as a lithium-based battery, a lead-acid battery, an alkaline battery, and/or another type of battery. That is, the one or more power supply units 342 can comprise one or more devices and/or circuitry configured to provide a source of power and/or provide power management functionality. Moreover, in some embodiments the one or more power supply units 342 include a mains power connector that is configured to couple to an alternating current (AC) or direct current (DC) mains power source.

The robotic system 110 can also include the one or more actuators/hardware 344 to facilitate movement of the robotic arms 112. Each actuator 344 can comprise a motor, which can be implemented in a joint or elsewhere within a robotic arm 112 to facilitate movement of the joint and/or a connected arm segment/linkage. Further, the robotic system 110 can include a variety of other components, such as pneumatics, optical sources, etc.

With reference to FIG. 3, the control system 130 and/or the robotic system 110 can include control circuitry 346 and/or data storage/memory 348 configured to perform functionality described herein. For ease of discussion and illustration, the control circuitry 346 and data storage 348 are shown in blocks between the control system 130 and the robotic system 110. It should be understood that, in many embodiments, the control system 130 and the robotic system 110 can include separate instances of the control circuitry 346 and the data storage 348. That is, the control system 130 can include its own control circuitry and data storage (e.g., to implement processing on the control system 130), while the robotic system 110 can include its own control circuitry and data storage (e.g., to implement processing on the robotic system 110). In many embodiments, any reference herein to control circuitry may refer to circuitry embodied in a robotic system, a control system, or any other component of a medical system, such as any component of the medical system 100 shown in FIG. 1.

Although the control circuitry 346 is illustrated as a separate component from other components of the control system 130/robotic system 110, it should be understood that any or all of the other components of the control system 130 and/or the robotic system 110 can be embodied at least in part in the control circuitry 346. For instance, the control circuitry 346 can include various devices (active and/or passive), semiconductor materials and/or areas, layers, regions, and/or portions thereof, conductors, leads, vias, connections, and/or the like, wherein one or more of the other components of the control system 130/robotic system 110 and/or portion(s) thereof can be formed and/or embodied at least in part in/by such circuitry components/devices.

As illustrated, the data storage 348 can include a collision component 350 configured to facilitate various functionality discussed herein. In some embodiments, the collision component 350 can include one or more instructions that are executable by the control circuitry 346 to perform one or more operations. Although many embodiments are discussed in the context of the collision component 350 including one or more instructions that are executable by the control circuitry 346, the collision component 350 (and/or other components, such as a localization component) can be implemented at least in part as one or more hardware logic components, such as one or more application specific integrated circuits (ASIC), one or more field-programmable gate arrays (FPGAs), one or more program-specific standard products (ASSPs), one or more complex programmable logic devices (CPLDs), and/or the like.

The collision component 350 can be configured to determine a collision region for an environment. For example, the collision component 350 can perform any of the operations discussed herein related to establishing a collision region associated with an object based on a position of a robotic arm 112 adjacent to the object. The collision component 350 can also use a collision region to control movement of the robotic system 110 and/or a medical instrument connected to the robotic system 110.

In some embodiments, the collision component 350 can adjust a collision region during a procedure. For example, if a collision region is determined for an object during setup of a procedure, and a robotic arm contacts an additional object and/or an additional edge of the object during the procedure, the collision component 350 can learn where an additional collision point is located and update the previously determined collision region to reflect the additional object/edge, such as by adding an additional boundary to the collision region, updating an existing boundary of the collision region, and so on.

Further, in some embodiments the collision component 350 can determine a collision region in another manner. In one example, a user can be asked to draw a bounding box on a user interface that is displaying information representing an environment, and the collision component 350 can formulate a collision region defined by the lines drawn by the user. In another example, a user can interact with a user interface to place a box or other shape on information that is displayed in the interface representing an environment. In a similar fashion, the collision component 350 can formulate a collision region for the box/shape. In yet another example, an imaging device/depth sensor can be placed on a distal end of a robotic arm to capture one or more images of an environment, and the collision component 350 can process the one or more images (e.g., with image/vision processing techniques) to identify one or more objects in the environment and/or a collision region for the one or more objects.

Although not illustrated in FIG. 3, in some embodiments the data storage 348 includes a localization component configured to perform one or more localization techniques to determine and/or track a position and/or an orientation of an object, such as a medical instrument connected to the robotic system 110. For example, the localization component can process input data, such as sensor data from a medical instrument (e.g., EM field sensor data, vision data captured by an imaging device/depth sensor on the medical instrument, accelerometer data from an accelerometer on the medical instrument, gyroscope data from a gyroscope on the medical instrument, satellite-based positioning data from a satellite-based sensor (a global positioning system (GPS), for example), and so on), robotic command and/or kinematics data for the robotic arms 112, sensor data from a shape sensing fiber (e.g., which can provide shape data regarding a location/shape of the medical instrument), model data regarding anatomy of a patient, position data of a patient, pre-operative data, etc. Based on such processing, the localization component can generate position/orientation data for a medical instrument. The position/orientation data can indicate a location and/or an orientation of the medical instrument relative to a frame of reference. The frame of reference can be a frame of reference relative to anatomy of a patient, a known object (e.g., an EM field generator), a coordinate system/space, and so on. In some implementations, position/orientation data can indicate a location and/or an orientation of a distal end of a medical instrument (and/or proximal end, in some cases). A position and orientation of an object can be referred to as a pose of the object.

In some implementations, the localization component can use electromagnetic tracking to determine a position and/or an orientation of an object. For example, the localization component can use real-time EM tracking to determine a real-time location of a medical instrument in a coordinate system/space that can be registered to the patient's anatomy, which can be represented by a pre-operative model or other model. In EM tracking, an EM sensor (or tracker) including one or more sensor coils can be embedded in one or more locations and/or orientations in a medical instrument (e.g., a scope, a needle, etc.). The EM sensor can measure a variation in an EM field created by one or more static EM field generators positioned at a known location. The location information detected by the EM sensors can be stored as EM data. The localization component can process the EM data to determine a position and/or orientation of an object, such as a medical instrument. An EM field generator (or transmitter) can be placed close to the patient (e.g., within a predetermined distance) to create a low intensity magnetic field that an EM sensor can detect. The magnetic field can induce small currents in the sensor coils of the EM sensor, which can be analyzed to determine a distance and/or angle between the EM sensor and the EM field generator. These distances and/or orientations can be intra-operatively "registered" to patient anatomy (e.g., a pre-operative model) in order to determine a geometric transformation that aligns a single location in a coordinate system with a position in the pre-operative model of the patient's anatomy. Once registered, an EM sensor (e.g., an embedded EM tracker) in one or more positions of a medical instrument (e.g., the distal tip of an endoscope, a needle, etc.) can provide real-time indications of a position and/or an orientation the medical instrument through the patient's anatomy.

The term "control circuitry" is used herein according to its broad and ordinary meaning, and can refer to any collection of one or more processors, processing circuitry, processing modules/units, chips, dies (e.g., semiconductor dies including come or more active and/or passive devices and/or connectivity circuitry), microprocessors, micro-controllers, digital signal processors, microcomputers, central processing units, graphics processing units, field programmable gate arrays, programmable logic devices, state machines (e.g., hardware state machines), logic circuitry, analog circuitry, digital circuitry, and/or any device that manipulates signals (analog and/or digital) based on hard coding of the circuitry and/or operational instructions. Control circuitry can further comprise one or more, storage devices, which can be embodied in a single memory device, a plurality of memory devices, and/or embedded circuitry of a device. Such data storage can comprise read-only memory, random access memory, volatile memory, non-volatile memory, static memory, dynamic memory, flash memory, cache memory, data storage registers, and/or any device that stores digital information. It should be noted that in embodiments in which control circuitry comprises a hardware state machine (and/or implements a software state machine), analog circuitry, digital circuitry, and/or logic circuitry, data storage device(s)/register(s) storing any associated operational instructions can be embedded within, or external to, the circuitry comprising the state machine, analog circuitry, digital circuitry, and/or logic circuitry.

The term "memory" is used herein according to its broad and ordinary meaning and can refer to any suitable or desirable type of computer-readable media. For example, computer-readable media can include one or more volatile data storage devices, non-volatile data storage devices, removable data storage devices, and/or nonremovable data storage devices implemented using any technology, layout, and/or data structure(s)/protocol, including any suitable or desirable computer-readable instructions, data structures, program modules, or other types of data.

Computer-readable media that can be implemented in accordance with embodiments of the present disclosure includes, but is not limited to, phase change memory, static random-access memory (SRAM), dynamic random-access memory (DRAM), other types of random access memory (RAM), read-only memory (ROM), electrically erasable programmable read-only memory (EEPROM), flash memory or other memory technology, compact disk read-only memory (CD-ROM), digital versatile disks (DVD) or other optical storage, magnetic cassettes, magnetic tape, magnetic disk storage or other magnetic storage devices, or any other non-transitory medium that can be used to store information for access by a computing device. As used in certain contexts herein, computer-readable media may not generally include communication media, such as modulated data signals and carrier waves. As such, computer-readable media should generally be understood to refer to non-transitory media.

Example Collision Region Determination

FIGS. 5-9 illustrate a top view the medical system 100 of FIG. 1 arranged in several configurations to determine a collision region in accordance with one or more embodiments. In these examples, the medical system 100 is arranged in an operating room to remove a kidney stone from the patient 120. In many embodiments, the patient 120 is positioned in a modified supine position with the patient 120 slightly tilted to the side to access the back or side of the patient 120, such as that illustrated. However, the patient 120 can be positioned in other manners, such as a supine position, a prone position, and so on. Although FIGS. 5-9 illustrate use of the medical system 100 to perform a percutaneous procedure to remove a kidney stone from the patient 120, as noted above, the medical system 100 can be used to remove a kidney stone in other manners and/or to perform other procedures. Various acts are described in FIGS. 5-9 and throughout this disclosure as being performed by the physician 140. It should be understood that these acts can be performed directly by the physician 140, a user under direction of the physician 140, another user (e.g., a technician), a combination thereof, and/or any other user.

The renal anatomy, as illustrated at least in part in FIGS. 5-9, is described here for reference with respect to certain medical procedures relating to aspects of the present concepts. The kidneys generally comprise two bean-shaped organs located on the left and right in the retroperitoneal space. In adult humans, the kidneys are generally about 11 cm in length. The kidneys receive blood from the paired renal arteries; blood exits into the paired renal veins. Each kidney is attached to a ureter, which is a tube that carries excreted urine from the kidney to the bladder. The bladder is attached to the urethra.

The kidneys are typically located relatively high in the abdominal cavity and lie in a retroperitoneal position at a slightly oblique angle. The asymmetry within the abdominal cavity, caused by the position of the liver, typically results in the right kidney being slightly lower and smaller than the left, and being placed slightly more to the middle than the left kidney. On top of each kidney is an adrenal gland. The upper parts of the kidneys are partially protected by the 11th and 12th ribs. Each kidney, with its adrenal gland is surrounded by two layers of fat: the perirenal fat present between renal fascia and renal capsule and pararenal fat superior to the renal fascia.

The kidney participates in the control of the volume of various body fluid compartments, fluid osmolality, acid-base balance, various electrolyte concentrations, and removal of toxins. The kidneys provide filtration functionality by secreting certain substances and reabsorbing others. Examples of substances secreted into the urine are hydrogen, ammonium, potassium, and uric acid. In addition, the kidneys also carry out various other functions, such as hormone synthesis, and others.

A recessed area on the concave border of the kidney is the renal hilum, where the renal artery enters the kidney and the renal vein and ureter leave. The kidney is surrounded by tough fibrous tissue, the renal capsule, which is itself surrounded by perirenal fat, renal fascia, and pararenal fat. The anterior (front) surface of these tissues is the peritoneum, while the posterior (rear) surface is the transversalis fascia.

The functional substance, or parenchyma, of the kidney is divided into two major structures: the outer renal cortex and the inner renal medulla. These structures take the shape of a plurality of cone-shaped renal lobes, each containing renal cortex surrounding a portion of medulla called a renal pyramid. Between the renal pyramids are projections of cortex called renal columns. Nephrons, the urine-producing functional structures of the kidney, span the cortex and medulla. The initial filtering portion of a nephron is the renal corpuscle, which is located in the cortex. This is followed by a renal tubule that passes from the cortex deep into the medullary pyramids. Part of the renal cortex, a medullary ray is a collection of renal tubules that drain into a single collecting duct.

The tip, or papilla, of each pyramid empties urine into a respective minor calyx; minor calyces empty into major calyces, and major calyces empty into the renal pelvis, which transitions to the ureter. At the hilum, the ureter and renal vein exit the kidney and the renal artery enters. Hilar fat and lymphatic tissue with lymph nodes surrounds these structures. The hilar fat is contiguous with a fat-filled cavity called the renal sinus. The renal sinus collectively contains the renal pelvis and calyces and separates these structures from the renal medullary tissue.

FIGS. 5-9 show various features of the anatomy of the patient 120. For example, the patient 120 includes kidneys 502 fluidly connected to a bladder 504 via ureters 506, and a urethra 508 fluidly connected to the bladder 504. As shown in the enlarged depiction of the kidney 502(A), the kidney 502(A) includes calyces (including calyx 510), renal papillae (including the renal papilla 512), and renal pyramids (including the renal pyramid 514). In these examples, a kidney stone 516 is located in proximity to the papilla 512. However, the kidney stone 516 can be located at other locations within the kidney 1502(A) or elsewhere. For ease of illustration, the enlarged depiction of the kidney 502(A) is not shown in FIGS. 6-9.

Figure 5:
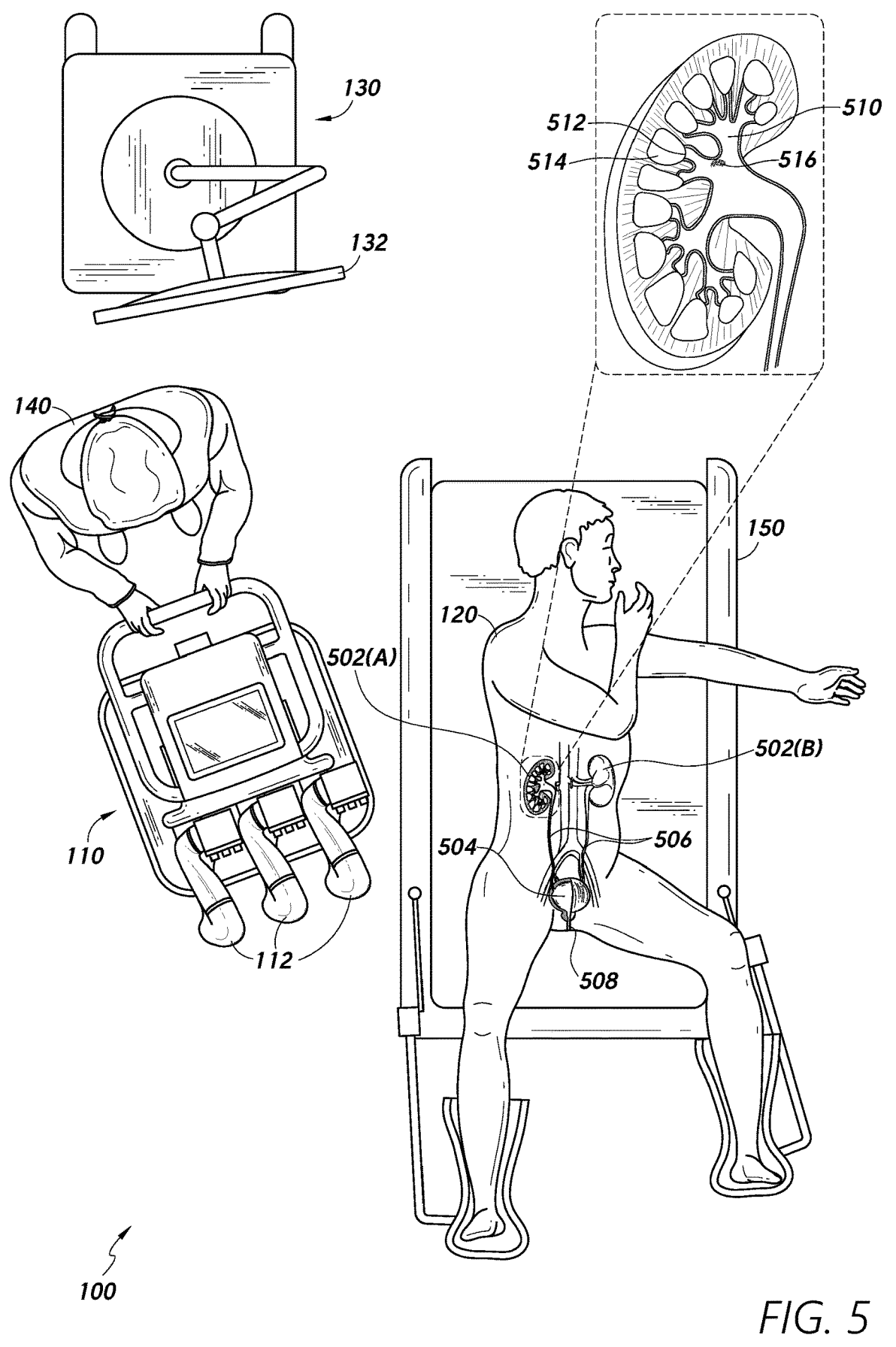
Figure 6:
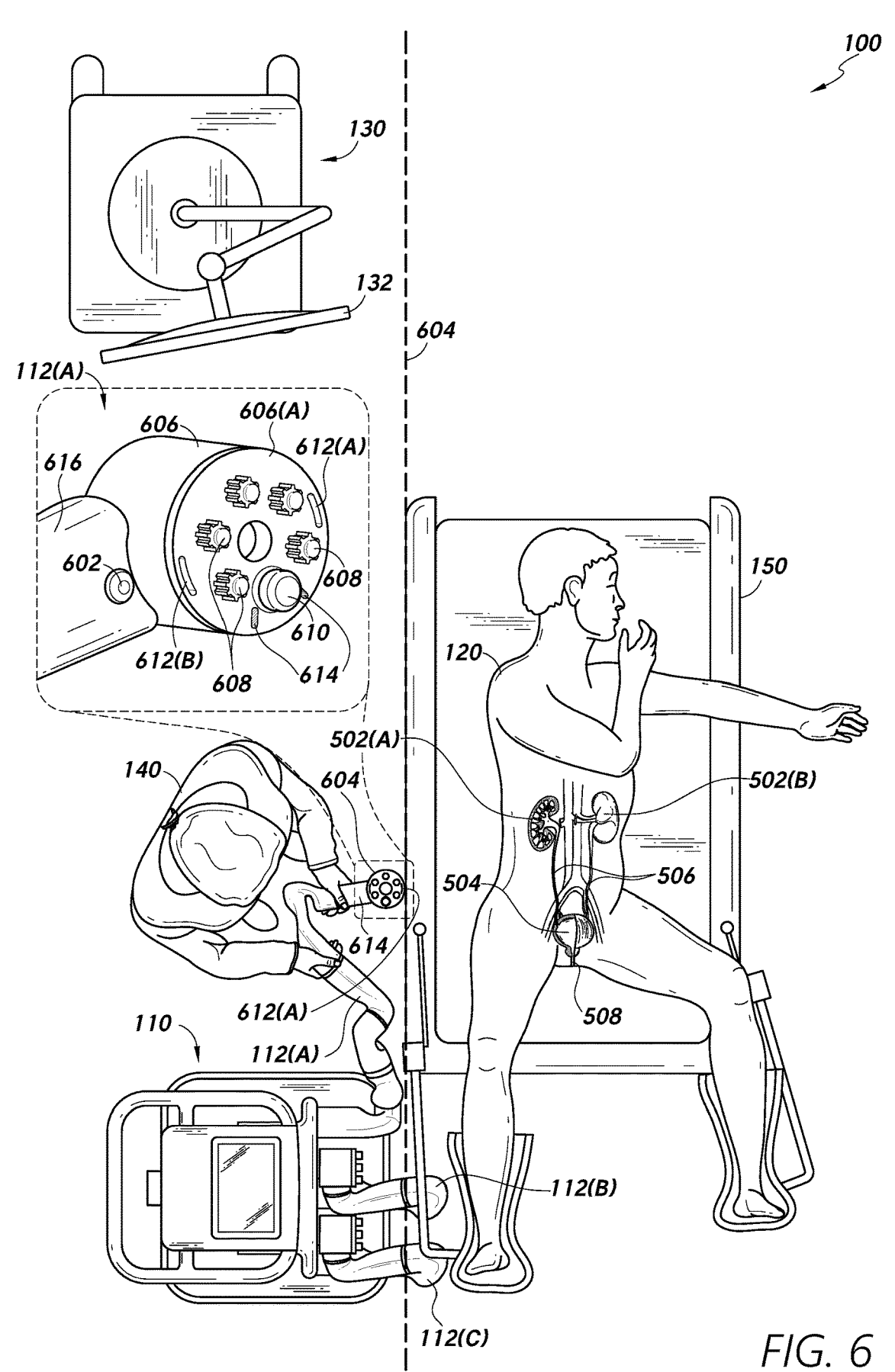
FIG. 6 illustrates a top view of the medical system of FIG. 5 as the physician positions a robotic arm adjacent to an object in accordance with one or more embodiments.

As shown in FIGS. 5 and 6, to remove the kidney stone 516 in the example percutaneous procedure, the physician 140 can move the robotic system 110 to the side/foot of the table 150 to setup/configure the robotic system 110. In particular, the robotic system 110 can be positioned at the side of the table 150 within proximity to the feet of the patient 120, as illustrated in FIG. 6. This can allow the robotic system 110 to be positioned for access to the urethra 508 of the patient 120. In examples, the hip of the patient 120 is used as a reference point to position the robotic system 110. While moving the robotic system 110, the robotic arms 112 can be positioned in a docked manner, similar to that shown in FIG. 5. However, the robotic arms can be positioned in any manner while moving the robotic system 110.

Once positioned at the foot of the table 150, as shown in FIG. 6, the robotic system 110 can be immobilized using wheel locks to hold the control system 130 in place. In examples, the location of the robotic system 110 in the environment is maintained throughout the procedure (e.g., the position of the robotic system 110 on the floor of the operating room). That is, the position of the robotic system 100 relative to the table 150 and/or other devices/medical equipment in the environment can be maintained throughout the procedure. Although the robotic system 110 is illustrated as being positioned at a particular location, the robotic system 110 can be positioned at other locations during setup and/or at other times during a procedure.

With reference to FIG. 6, the physician 140 can manually move the robotic arm 112(A) to a first edge of the table 150. In this example, the physician 140 presses a button 602 located on a distal end of the robotic arm 112(A) to manually move the robotic arm 112(A) adjacent to the table 150. For instance, the physician 140 can press the button 602 to enable an admittance control mode in which the robotic arm 112(A) can be manually moved. In examples, the physician 140 is allowed to move the robotic arm 112(A) (e.g., the admittance control mode is enabled) as long as the button 602 is pressed. However, the admittance control mode can be enabled through other types of input. Further, the robotic arm 112(A) can be moved without enabling/disabling an admittance control mode (e.g., the robotic arm 112(A) can always be configured for manual movement). In some embodiments, the physician 140 can navigate to a set up interface on the control system 130 and/or the robotic system 110, wherein the interface can instruct the physician 140 to position one or more of the robotic arms 112 adjacent to an object in the environment to detect a surrounding of the robotic system 110.

In some embodiments, when the robotic arm 112(A) is positioned at the first edge of the table 150, the physician 140 can provide input indicating that the robotic arm 112(A) is positioned adjacent to an object within the environment. Here, the control system 130 can receive position information from the robotic system 110 indicating a position of the robotic arm 112(A). Alternatively, or additionally, in some embodiments, the robotic system 110 can notify the control system 130 that the robotic arm 112(A) is positioned adjacent to an object (and send position information regarding the robotic arm 112(A)) when the physician 140 releases the button 602 (and/or after a predetermined period of time has passed from releasing the button 602). In any event, the control system 130 can use position information regarding the robotic arm 112(A) to determine a position of a distal end of the robotic arm 112(A), such as a position of the distal end of the robotic arm 112(A) within the environment, a position of the distal end of the robotic arm 112(A) relative to the rest of the robotic system 110, a position of the distal end of the robotic arm 112(A) relative to the control system 130, and so on.

Based on the position of the distal end of the robotic arm 112(A), the control system 130 can define a plane/boundary 604 (also referred to as "the first plane 604"), such as a plane tangent to the distal end of the robotic arm 112(A). In some embodiments, a component/marking on an end effector/IDM 606 of the robotic arm 112(A) can be used as an alignment/ reference point for the plane (e.g., a component/marking on the robotic arm 112(A), a particular face of the end effector 606 (a front face, for example), etc.). For instance, as shown in the enlarged image of the distal end of the robotic arm 112(A), the end effector 606 of the robotic arm 112(A) can include multiple gears 608 to control/articulate a medical instrument, a reader 610 to read data from a medical instrument (e.g., radio-frequency identification (RFID) reader to read a serial number from a medical instrument), fasteners 612 to attach a medical instrument to the IDM 606 (e.g., latches to secure the medical instrument), markers 614 to align with an instrument that is manually attached to a patient (e.g., an access sheath) and/or to define a front surface of the IDM 606. In the example of FIG. 6, the fastener 612 (A) is used to define a plane tangent to the end effector 606 of the robotic arm 112(A). In some embodiments, a portion 606(A) of the end effector 606 can be configured to rotate/spin, such as by a user when the robotic arm 112(A) is operating in the admittance control mode. For example, the physician 140 can move the robotic arm 112(A) to a desired position and then rotate the top plate 606(A) of the IDM 606 to the orientation shown in FIG. 6 to determine the orientation of the plane 604. As such, the physician 140 can be instructed to align the fastener 612(A) (or one of the fasteners 612) with the edge of the table 150 (e.g., rotate the portion 606(A)). However, any component/ marking on the end effector 606 can be used as a reference point. Further, in some embodiments, a plane can be defined with respect to a linkage segment of the robotic arm 112(A), such as perpendicular to a most distal linkage segment 616 of the robotic arm 112(A) (and/or tangent to the end effector 606). In examples, the control system 130 can define a plane/boundary for a collision region based on information indicating one or more dimensions of the robotic arm 112(A) and/or the end effector 606, which can be maintained/ received by the control system 130.

Figure 7:
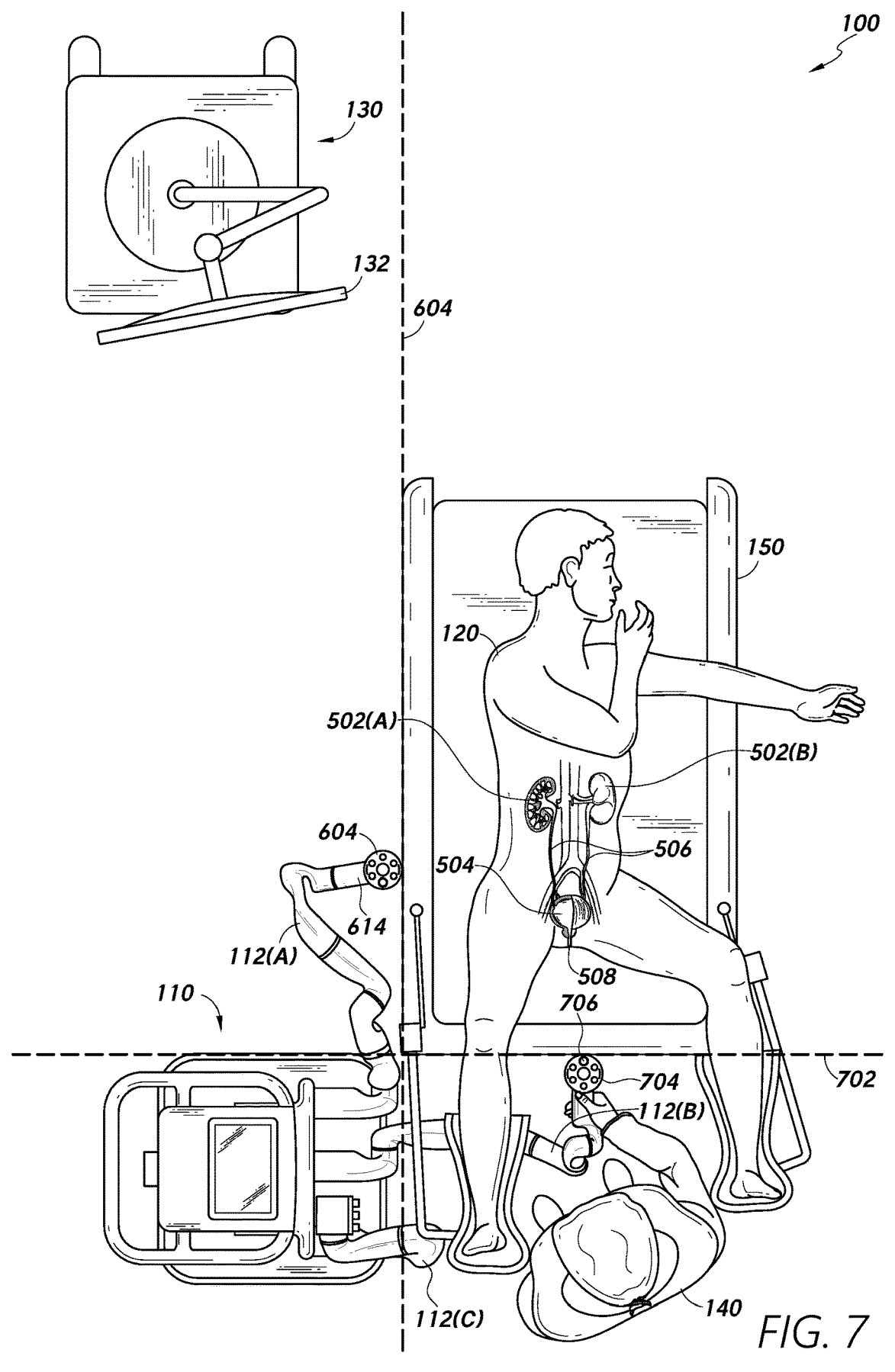
FIG. 7 illustrates a top view of the medical system of FIG. 5 as the physician positions another robotic arm adjacent to the object in accordance with one or more embodiments.

FIG. 7 illustrates an example where the robotic arm 112(B) (also referred to as "the second robotic arm 112(B)") is positioned adjacent to a second edge of the table 150 to determine a plane/boundary 702 (also referred to as "the second plane 702"). In a similar fashion as that described above with respect to the robotic arm 112(A) (also referred to as "the first robotic arm 112(A)"), the physician 140 can manually move a distal end of the second robotic arm 112(B) adjacent to the second edge of the table 150 (e.g., the foot of the table 150). As illustrated, an end effector 704 of the second robotic arm 112(B) can be positioned adjacent to the second edge of the table 150 and the control system 130 can define the second plane 702 based on the position of the end effector 704 of the second robotic arm 112(B). In this example, the second plane 702 is established to be tangent to the end effector 704 at a connection element 706. The physician 140 may be instructed to position the second robotic arm 112(B) relative to the connection element 706. However, other components/markings of the second robotic arm 112(B) can be used.

Figure 8:
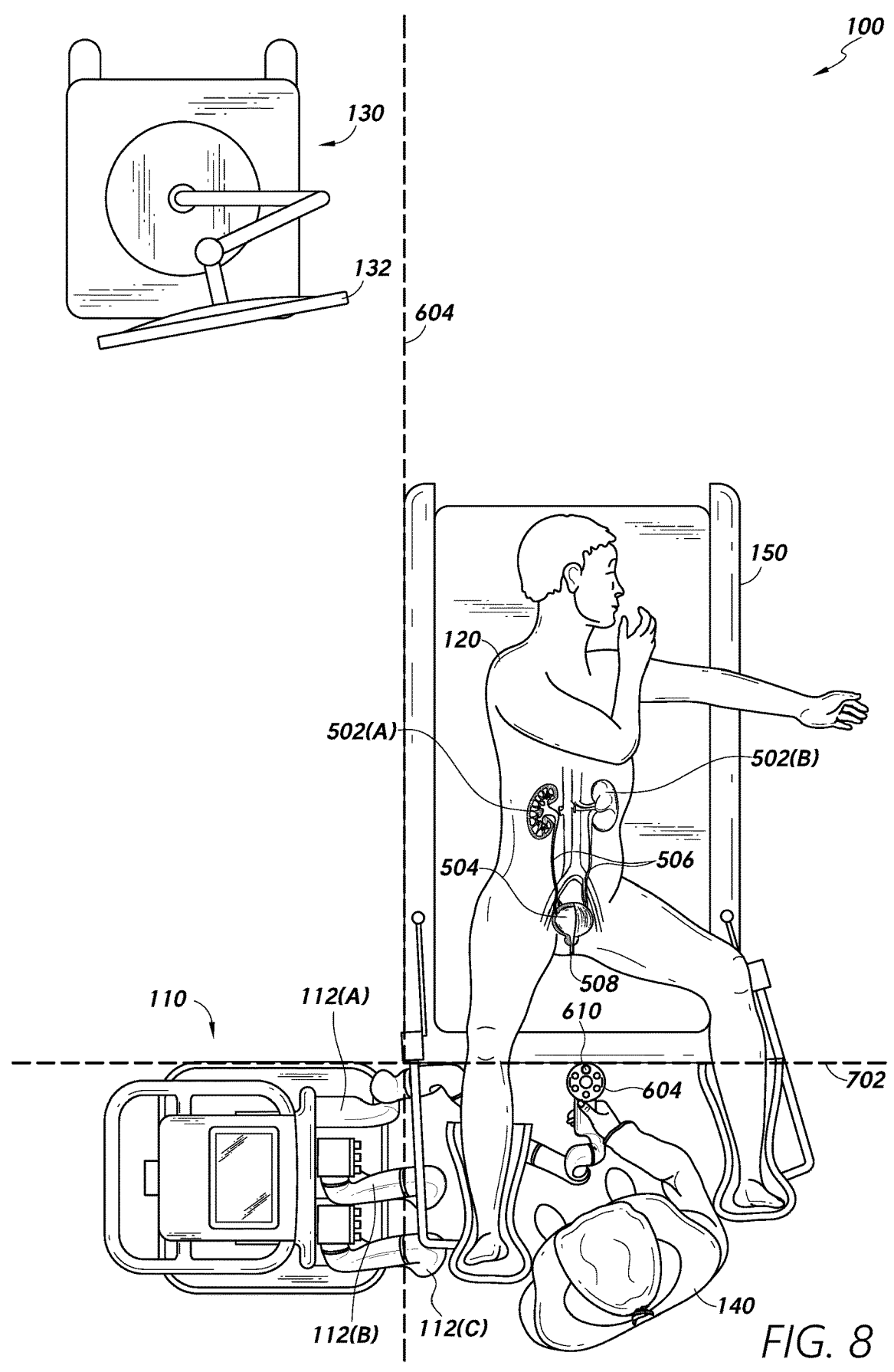
FIG. 8 illustrates a top view of the medical system of FIG. 5 in an alternative example where the physician positions the robotic arm adjacent to the object at an additional position in accordance with one or more embodiments.

FIG. 8 illustrates an alternative example where the first robotic arm 112(A) is positioned adjacent to the second edge of the table 150 to determine the second plane/boundary 702. In a similar fashion as that described above with respect FIG. 6, the physician 140 can manually move the distal end of the first robotic arm 112(A) adjacent to the second edge of the table 150. As illustrated, the end effector 604 of the first robotic arm 112(A) can be positioned adjacent to the second edge of the table 150 and the control system 130 can define the second plane 702 based on the position of the end effector 604 of the first robotic arm 112(A). In this example, the second plane 702 is formed to be tangent to the end effector 604 at the reader 610. However, other components/markings of the first robotic arm 112(A) can be used. In some embodiments, the first robotic arm 112(A) is positioned adjacent to the second edge of the table 150 after the first robotic arm 112(A) is positioned adjacent to the first edge of the table 150.

Figure 9:
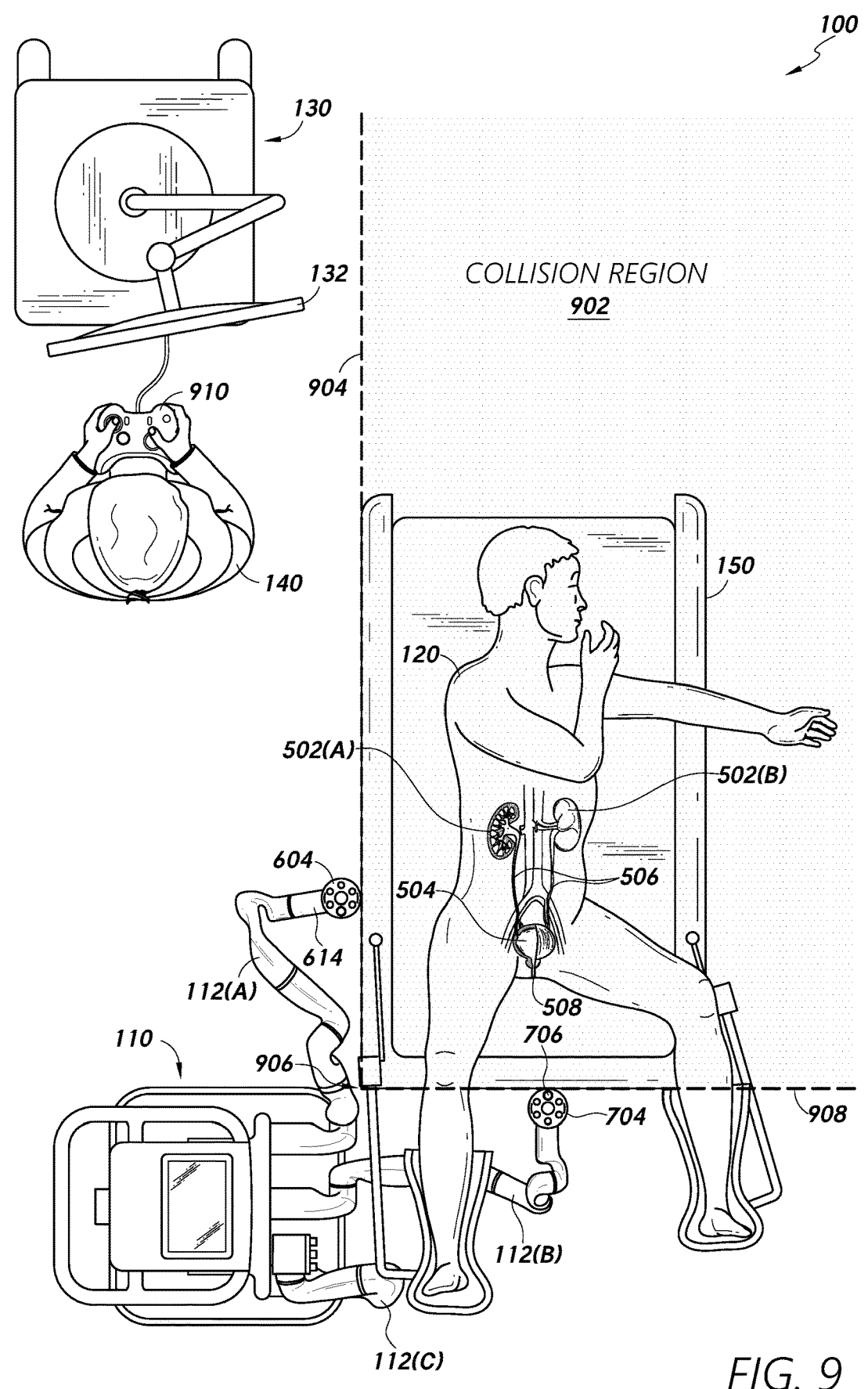
FIG. 9 illustrates a top view of the medical system of FIG. 5 with a collision region in accordance with one or more embodiments.

In either example, the control system 130 can determine a collision region 902 based on the first plane 604 and the second plane 702 as illustrated in FIG. 9. For example, the control system 130 can define a first boundary 904 for the collision region 902 based on the first plane 604 and an intersection 906 of the first plane 604 and the second plane 702. The first boundary 904 can extend from the intersection 906 upwards with respect to FIG. 9. Further, the control system 130 can define a second boundary 908 for the collision region 902 based on the second plane 702 and the intersection 906 of the first plane 604 and the second plane 702. The second boundary 908 can extend from the intersection 906 to the right with respect to FIG. 9. The boundaries 904 and 908 can extend any distance from the intersection 906 (e.g., encompassing an area substantially larger than the table 150 and/or the patient 120, encompassing just the table 150, etc.). For instance, the boundaries 904 and/or 908 can extend a distance that is associated with a dimension of the table 150, such as a known length, height, and/or depth of the table 150 (or another object), an average length, height, and/or depth of a table (or another object), and so on. The control system 130 can define the collision region 902 to exclude the robotic arms 112, such as the robotic arms 112(A) and 112(B) that are positioned adjacent to the table 150. In examples, the collision region 902 can include a three-dimensional (3D) form, such as that illustrated in FIG. 2.

In some embodiments, upon determining the collision region 902, the control system 130 can output information representing the collision region 902. For example, the display(s) 132 can present a visualization of the collision region 902 via an interface, such as the interface illustrated in FIG. 10. The interface can enable the physician 140 to accept the collision region 902 and/or adjust/reconfigure the collision region 902, as discussed in further detail below. The physician 140 can interact with the interface via an I/O device, such as a hand-held controller 910, the display(s) 132 (e.g., touchscreen), or any other I/O device. Upon accepting the collision region 902, the control system 130 can configure the robotic system 110 to perform a procedure based on the collision region 902, such as by designating the collision region 902 as associated with one or more objects that can cause collisions.

The collision region 902 can be used to perform a procedure in a manner that generally seeks to avoid collisions with objects in the environment. For example, one or more medical instruments can be connected to one or more of the robotic arms 112 of the robotic system 110 and the one or more robotic arms 112 can be positioned in a manner suitable for the procedure. The physician 140 can facilitate/manage/control of the procedure from the convenience of the control system 130 (e.g., with the physician 140 positioned as shown in FIG. 9). For instance, the physician 140 can interact with an I/O device of the control system 130, such as the hand-held controller 910, to provide user input to control the one or more medical instruments attached to the robotic system 110. The base of the robotic system 110 can remain stationary during the procedure, while the robotic arms 112 are moved in different manners to control the one or more medical instruments.

During the procedure, the control system 130 can process user input from the physician 140 to control movement of the robotic arms 112, so that the robotic arms 112 and/or the attached medical instruments generally move within the environment outside the collision region 902. To illustrate, the robotic arm 112(A) can be controlled to move within the environment without the robotic arm 112(A) and/or an attached medical instrument crossing the first boundary 904 and/or the second boundary 908. In examples, the control system 130 can account for one or more dimensions/shape of the medical instrument and/or an orientation of the medical instrument on the robotic arm 112(A). In some embodiments, the control system 130 and/or the robotic system 110 can provide an alert to the physician 140, such as via the display(s) 132, if user input would cause movement into the collision region 902. The physician 140 can, if desired, override the configuration of the robotic system 110/control system 130 to cause the robotic arm 112 to move into the collision region 902. Further, in some embodiments, the movement of the robotic arms 112 can be controlled in other manners based on the collision region 902. In examples, the physician 140 can manually move one or more of the robotic arms 112 into the collision region 902 or elsewhere in the environment by enabling the admittance control mode.

In the examples of FIGS. 5-9, the robotic arms 112 are positioned adjacent to the table 150 without medical instruments coupled thereto. However, in some embodiments, the robotic arms 112 can be positioned adjacent to an object with one or more medical instruments attached thereto. In such embodiments, the control system 130 can use a reference point on a medical instrument and/or information regarding one or more dimensions of the medical instrument to define a plane/boundary for a collision region.

Further, the examples of FIGS. 5-9 illustrate a collision region that is determined by positioning one or two of the robotic arms 112 at two positions adjacent to the table 150. It should be understood that one or more of the robotic arms 112 can be positioned at more than two positions (or just one position) adjacent to the table 150 and/or other objects within the environment. As such, the collision region can have any number of surfaces/planes/points. In one illustration, the robotic arm 112(C) (also referred to as "the third robotic arm 112(C)") can be positioned adjacent to the foot of the table 150, similar to the second robotic arm 112(B) illustrated in FIG. 9. Here, the third robotic arm 112(C) can assist in accurately defining the second boundary 908 of the collision region 902 (e.g., a plane/surface that is tangent to both robotic arms 112(B) and 112(C)). In another illustration, the third robotic arm 112(C) (and/or any other robotic arm 112) can establish a height of the table 150, position of the patient 120 (e.g., legs of the patient 120 that extend beyond the bed), etc. In yet another illustration, a collision region can include a single boundary/plane, such as a region that includes the table 150 and is defined by just the plane 604, as illustrated in FIG. 6.

In some embodiments, the techniques can allow the robotic system 110 to be used at a convenient/desired location in an environment and avoid collisions with objects in the workspace of the robotic system 110 at that location. For instance, the robotic system 110 can be positioned anywhere within an environment and then used to detect locations of objects in the environment. For ease of discussion, many operations are discussed in the context of being performed by control system 130, such as determining a position of a robotic arm, determining a collision region, and so on, such operations can alternatively, or additionally, be performed by the robotic system 110 and/or another device/system.

Example Interface

Figure 10:
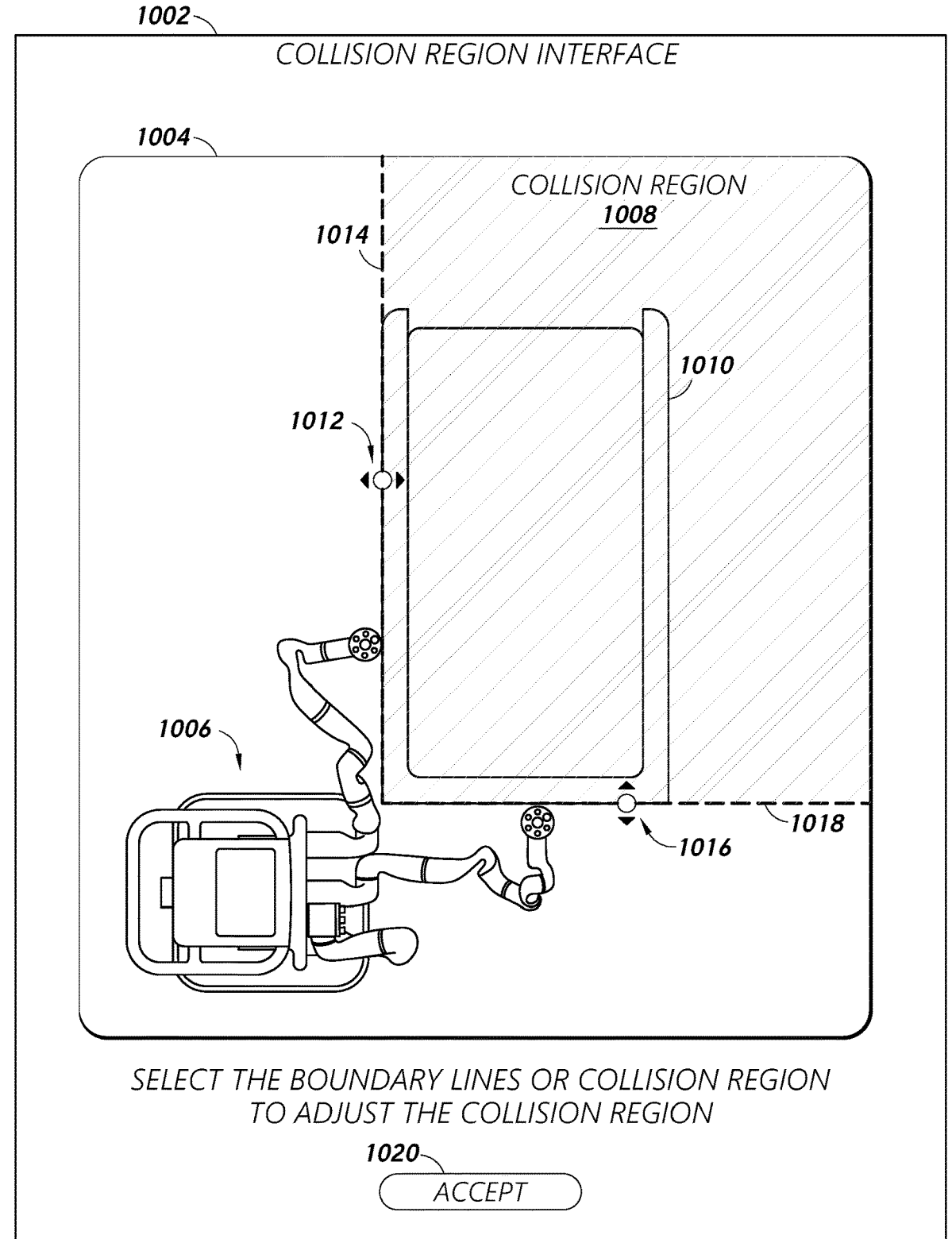
FIG. 10 illustrates an example interface to visualize and/or configure a collision region in accordance with one or more embodiments.

FIG. 10 illustrates an example interface 1002 to visualize and/or configure a collision region in accordance with one or more embodiments. In examples, the interface 1002 can be displayed via the control system 130, the robotic system 110, and/or any other device of the medical system 100. For instance, the interface 1002 can be displayed via the control system 130 to enable the physician 140 to view a collision region that is determined for an environment in which the robotic system 110 is located and/or provide adjustment input data to reconfigure the collision region and/or other elements in the environment.

As shown, the interface 1002 can present a visualization 1004 regarding the environment in which the robotic system 110 is located. The visualization 1004 can include a visual representation 1006 (e.g., icon or other user interface element) of the robotic system 110, a visual representation 1008 of a collision region determined for the environment, and a visual representation 1010 of the table 150 located within the environment. The visualization 1004 can be based upon position/orientation information of the robotic system 110, information regarding a position/orientation of the collision region 1008, information regarding the table 150 (e.g., estimated/actual dimensions of the table 150), and/or any other information regarding the environment.

The interface 1002 can enable a user to accept and/or configure the collision region. For example, the user can select a user interface element 1012 to adjust a first boundary 1014 of the collision region 1008 and/or select a user interface element 1016 to adjust a second boundary 1018 of the collision region 1008. For example, the user can select and drag the interface element 1012/1016 to a desired location to change a position/orientation of the boundary 1014/1018, which can increase/decrease a size of the collision region 1008 (and the associated collision region for the environment), change a shape of the collision region 1008 (and the associated collision region for the environment), etc. For example, the user can move the second boundary 1018 to extend beyond the bottom edge of the table 1010, so that the collision region 1008 encompasses a portion of a patient (not illustrated) that extends beyond the bottom edge of the table 150. Further, in some examples, the user can select and drag the collision region 1008 to another location. In examples, the user can manipulate the collision region 1008, the visual representation 1006 of the robotic system

110, and/or the visual representation 1010 of the table 150 to change any characteristic, such as to remove a boundary, reposition/reorient the visual representation 1006/1008/1010 (which can cause the control system 130/the robotic system 110 to update the associated position/orientation information for the environment), and so on. When the collision region 1008 (and/or other elements of the visualization 1004) are acceptable to the user, the user can select a button 1020 to accept the configuration and cause the control system 130/the robotic system 110 to configure the medical system 100 to operate based on the configuration (e.g., the associated collision region).

Example Flow Diagram

Figure 11:
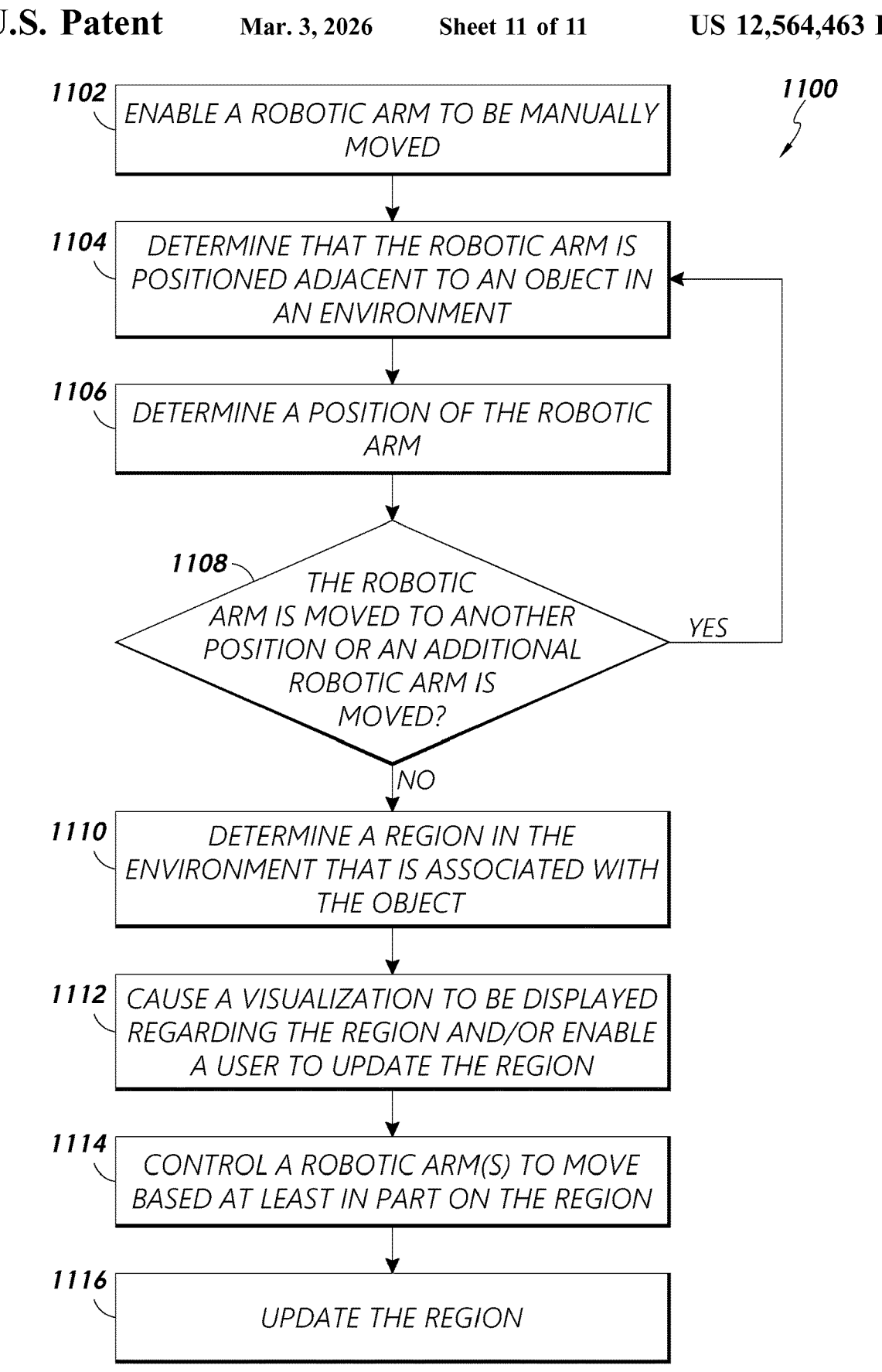
FIG. 11 illustrates an example flow diagram of a process for determining a region associated with an object in accordance with one or more embodiments.

FIG. 11 illustrates an example flow diagram of a process 1100 for determining a region associated with an object in accordance with one or more embodiments. The various operations/acts associated with the process 1100 can be performed by control circuitry implemented in any of the devices/systems discussed herein or a combination thereof, such as the control system 130, the robotic system 110, the table 150, a medical instrument, and/or another device. The process 1100 can be performed during setup/configuration of the medical system 100 for a procedure, during a procedure, after a procedure, and/or at other times. In one illustration, the process 1100 is performed to configure the robotic system 110 for a procedure. Although various blocks are illustrated as being part of the process 1100, any of such blocks can be eliminated. Further, additional blocks can be implemented as part of the process 1100. The order in which the blocks are illustrated is provided merely for illustrative purposes, and the blocks can be implemented in any order. In some embodiments, one or more of the blocks of the process 1100 are implemented as executable instructions, that when executed by control circuitry, cause the control circuitry to perform the functionality/operations discussed. However, one or more of the blocks of the process 1100 can be implemented in other manners, such as by other devices/systems, a user(s), etc.

At block 1102, the process 1100 can include enabling a robotic arm to be manually moved. For example, a user can provide input to set the robotic arm to an admittance control mode in which user manipulation of the robotic arm moves the robotic arm. The input can be provided in a variety of manners, such as by selecting a button on the robotic arm, providing input via an interface/controller, and so on. In some embodiments, the robotic arm can be enabled for manual movement upon entering a set up mode on a robotic system associated with the robotic arm, a control system, and/or another device/system. Although the operation 1102 is illustrated in the process 1100, in some embodiments the robotic arm can include a default/permanent state to allow manual movement of the robotic arm (e.g., block 1102 is not implemented).

At block 1104, the process 1100 can include determining that the robotic arm is positioned adjacent to an object in an environment. For example, the robotic arm can be determined to be adjacent to the object when input data is received (from an I/O device) indicating that the robotic arm is positioned adjacent to the object, the user releases a button on the robotic arm to disable an admittance control mode, the robotic arm remains stationary for a period of time after being moved (and/or after the user releases the button on the robotic arm), a combination thereof, and/or other events. In some embodiments, the robotic arm can be referred to as being positioned adjacent to the object when the robotic arm is contacting the object or otherwise positioned within proximity to the object, such as within a predetermined distance to the object.

At block 1106 the process 1100 can include determining a position of the robotic arm. For example, the control system/robotic system can use position data for the robotic arm to determine the position of an end of the robotic arm, such as a distal end of the robotic arm. The position information can indicate a position of an end-effector end of the robotic arm, such as an end that is configured to couple to a medical instrument.

At block 1108, the process 1100 can include determining if the robotic arm is moved to another position or determining if an additional robotic arm is moved. If the robotic arm is moved to another position or the additional robotic arm is moved to a position, the process 1100 can return to block 1104. For example, if the robotic arm is moved to another position, the process 1100 can return to block 1104 and determine that the robotic arm is positioned adjacent to another edge of the object and, at block 1106, determine the position of the robotic arm at the other edge of the object. Further, if an additional robotic arm is moved to a position, the process 1100 can return to block 1104 and determine that the additional robotic arm is positioned adjacent to the object and, at block 1106, determine the position of the additional robotic arm at the position adjacent to the object. The process 1100 can loop through the blocks 1104-1108 any number of times to determine position information associated with any number of reference points for the object.

At block 1110, the process 1100 can include determining a region/area in the environment that is associated with the object. For example, the region (also referred to as a "collision region" or "object region") can be determined based on a position of a distal end of a first robotic arm at a first reference point (e.g., at a first time), a position of a distal end of the first robotic arm at a second reference point (e.g., at a second time), a position of a distal end of a second robotic arm at a third reference point, a position of a distal end of the second robotic arm at a fourth reference point, and so on. The region can be based on position information for any number of robotic arms at any number of reference points for the object. In some embodiments, a boundary of the region can be determined based on a position of a distal end of a robotic arm. In one illustration, the region can be determined by defining a first plane based on a position of an end of a first robotic arm and defining a second plane based on a position of an end of a second robotic arm and/or a position of the end of the first robotic arm at a second time. Here, the region can be based on the first plane, the second plane, and an intersection of the first plane with the second plane. The region can include the object and/or exclude the robotic system.

At block 1112, the process 1100 can include causing a visualization regarding the region to be displayed and/or enabling a user to update the region. For example, interface data representing the visualization can be sent for display and/or the interface data can be displayed via a display(s) associated with the control system/robotic system. Adjustment input data can be received including an adjustment to the visual representation, and/or the region can be updated based on the adjustment to the visual representation (e.g., the adjustment data).

At block 1114, the process 1100 can include controlling one or more robotic arms to move based at least in part on the region. For example, a robotic arm of the robotic system can be controlled to move in the environment without moving within the region, to move into the region upon receiving confirmation from a user, etc. To illustrate, the control system/the robotic system can receive, from an input device, input control data regarding movement of a medical instrument attached to a robotic arm. The control system/the robotic system can determine that the input control data is associated with movement of the robotic arm into/within the collision region. The control system/the robotic system can cause a notification/alert to be displayed indicating that the input control data is associated with movement into the collision region. The control system/the robotic system can then receive input data (e.g., based on user input from the user) indicating whether or not to proceed into the collision region. The control system/the robotic system can proceed to move or refrain from moving the robotic arm into the collision region based on the input data. Alternatively, in some cases, the control system/the robotic system can prevent movement into the collision region without notifying/alerting the user and/or perform other processing without notifying/alerting the user.

At block 1116, the process 1100 can include updating the region. For example, the control system/the robotic system can be set to a procedure mode to perform a medical procedure. If, during the procedure, the control system/the robotic system determines that a robotic arm experienced a collision, the control system/the robotic system can update the region based on a position a distal end of the robotic arm when the collision occurred. In examples, a visualization of the region can be displayed during the procedure before the region is updated, similar to that discussed for block 1112.

In some embodiments, the region can be updated at any time before, during, or after a procedure, which may or may not include displaying a visualization of the region to the user. For example, blocks 1112 and/or 1116 can be performed at any time before, during, and/or after a procedure. In one illustration, an additional object can be brought into the environment (e.g., additional medical equipment can be moved within proximity to the robotic system during a procedure), and the region can be updated through to avoid collisions with the additional object.

Further, in some embodiments, one or more of the blocks of the process 1100 can be performed while the robotic system is located at a same parked position, such as a stationary position where one or more wheels for the robotic system are immobilized.

ADDITIONAL EMBODIMENTS

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is understood with the context as used in general to convey that an item, term, element, etc. may be either X, Y, or Z. Thus, such conjunctive language is not generally intended to imply that certain embodiments require at least one of X, at least one of Y, and at least one of Z to each be present.

It should be appreciated that in the above description of embodiments, various features are sometimes grouped together in a single embodiment, figure, or description thereof for the purpose of streamlining the disclosure and aiding in the understanding of one or more of the various aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the disclosure herein disclosed and claimed below should not be limited by the particular embodiments described above, but should be determined by a fair reading of the claims that follow.

It should be understood that certain ordinal terms (e.g., "first" or "second") may be provided for ease of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited.

Unless otherwise defined, all terms (including technical and scientific terms) used herein have the same meaning as commonly understood by one of ordinary skill in the art to which example embodiments belong. It be further understood that terms, such as those defined in commonly used dictionaries, should be interpreted as having a meaning that is consistent with their meaning in the context of the relevant art and not be interpreted in an idealized or overly formal sense unless expressly so defined herein.

The spatially relative terms "outer," "inner," "upper," "lower," "below," "above," "vertical," "horizontal," and similar terms, may be used herein for ease of description to describe the relations between one element or component and another element or component as illustrated in the drawings. It be understood that the spatially relative terms are intended to encompass different orientations of the device in use or operation, in addition to the orientation depicted in the drawings. For example, in the case where a device shown in the drawing is turned over, the device positioned "below" or "beneath" another device may be placed "above" another device. Accordingly, the illustrative term "below" may include both the lower and upper positions. The device may also be oriented in the other direction, and thus the spatially relative terms may be interpreted differently depending on the orientations.

Unless otherwise expressly stated, comparative and/or quantitative terms, such as "less," "more," "greater," and the like, are intended to encompass the concepts of equality. For example, "less" can mean not only "less" in the strictest mathematical sense, but also, "less than or equal to."

What is claimed is:
1. A method comprising:
enabling a first robotic arm to be moved within an environment;
determining, by control circuitry, that an end of the first robotic arm is in a first position adjacent to one or more objects in the environment;
determining a first plane within the environment based on the first position;
determining, by the control circuitry, that a second robotic arm is in a second position adjacent to the one or more objects;
determining a second plane within the environment based on the second position;
determining, by the control circuitry, a collision region associated with the one or more objects, the collision region including at least a first boundary that extends in a first direction from an intersection of the first plane with the second plane; and
controlling, by the control circuitry, movement of at least one of the first robotic arm or the second robotic arm within the environment, while avoiding the collision region, during a medical procedure.
2. The method of claim 1, wherein the first robotic arm is enabled to be moved manually, wherein determining that the end of the first robotic arm is in the first position is based on receiving first user input, and wherein determining that the second robotic arm is in the second position is based on receiving second user input.
3. The method of claim 1, wherein the first plane is tangent to the end of the first robotic arm, wherein the collision region further includes a second boundary that extends in a second direction from the intersection of the first plane with the second plane, the second direction being different than the first direction, and wherein the second plane is tangent to the end of the second robotic arm.
4. The method of claim 1, further comprising:
determining that the end of the first robotic arm is in a second position adjacent to the one or more objects, wherein the collision region is further determined based at least in part on the second position of the end of the first robotic arm.
5. The method of claim 4, wherein the second position determines a third plane within the environment, and wherein the collision region is determined based on the first plane, the second plane, and the third plane.
6. The method of claim 1, wherein at least one of the first robotic arm or the second robotic arm is configured to connect to a medical instrument, the method further comprising:
receiving, from an input device, input control data regarding movement of the medical instrument; and
determining that the input control data is associated with movement of at least one of the first robotic arm or the second robotic arm into the collision region.
7. The method of claim 6, further comprising:

causing a notification to be displayed indicating that the input control data is associated with movement into the collision region; and receiving user input indicating whether or not to proceed into the collision region, wherein controlling the movement of the at least first robotic arm or second robotic arm is based at least in part on the user input.

8. The method of claim 2, wherein the first and second robotic arms are connected to a robotic system, and the receiving of the first and second user inputs and the controlling of the movement of the at least first robotic arm or second robotic arm occur while the robotic system is located at a same parked position.

9. The method of claim 1, wherein the end of the first robotic arm is an end-effector end of the first robotic arm.

10. A control system comprising:

a communication interface configured to communicate with a first robotic arm and a second robotic arm; and control circuitry communicatively coupled to the communication interface and configured to:

determine that an end of the first robotic arm is in a first position adjacent to one or more objects in an environment;

determine a first plane within the environment based on the first position;

determine that the second robotic arm is in a second position adjacent to the one or more objects;

determine a second plane within the environment based on the second position;

determine a collision region associated with the one or more objects, the collision region including at least a first boundary that extends in a first direction from an intersection of the first plane with the second plane; and control movement of at least one of the first robotic arm or the second robotic arm within the environment, while avoiding the collision region, during a medical procedure.

11. The control system of claim 10, wherein at least one of the first robotic arm or the second robotic arm is configured to connect to a medical instrument, and wherein the control circuitry is further configured to:

receive, from an input device, input control data regarding movement of the medical instrument; and determine that the input control data is associated with movement of at least one of the first robotic arm or the second robotic arm into the collision region.

12. The control system of claim 10, wherein the control circuitry is further configured to:

determine that the second robotic arm is in a second position adjacent to the one or more objects, the second position determining a third plane within the environment, wherein the collision region is further determined based at least in part by the third plane.

13. The control system of claim 10, wherein the first plane is tangent to the end of the first robotic arm, wherein collision region further includes a second boundary that extends in a second direction from the intersection of the first plane with the second plane, the second direction being different than the first direction, and wherein the second plane is tangent to the end of the second robotic arm.

14. The control system of claim 10, wherein the control circuitry is further configured to:

display a visual representation of the collision region;

receive adjustment input data including an adjustment to the visual representation; and update the visual representation of the collision region based at least in part on the adjustment input data.

15. The control system of claim 10, wherein the control circuitry is further configured to:

set the control system to a procedure mode to perform a medical procedure;

determine that at least one of the first robotic arm or the second robotic arm experienced a collision; and update the collision region based on at least one of a position of the end of the first robotic arm when the collision occurred or a position of the second robotic arm when the collision occurred.

16. One or more non-transitory computer-readable media storing computer-executable instructions that, when executed by control circuitry, cause the control circuitry to perform operations comprising:

determining that an end of a first robotic arm is in a first position adjacent to one or more objects in an environment;

determining a first plane within the environment based on the first position;

determining that a second robotic arm is in a second position adjacent to the one or more objects;

determining a second plane within the environment based on the second position;

determining a collision region associated with the one or more objects, the collision region including at least a first boundary that extends in a first direction from an intersection of the first plane with the second plane; and control movement of at least one of the first robotic arm or the second robotic arm within the environment, while avoiding the collision region, during a medical procedure.

17. The one or more non-transitory computer-readable media of claim 16, wherein the operations further comprise:

determining that the second robotic arm is in a second position adjacent to the one or more objects, the second position determining third plane within the environment, wherein the collision region is further determined based at least in part by the third plane.

18. The one or more non-transitory computer-readable media of claim 16, wherein the collision region further includes a second boundary that extends in a second direction from the intersection of the first plane with the second plane, the second direction being different than the first direction.

19. The one or more non-transitory computer-readable media of claim 16, wherein the operations further comprise:

determining that that the end of the first robotic arm is in a second position adjacent to the one or more objects, wherein the collision region is further determined based at least in part on the second position of the end of the first robotic arm.

20. The one or more non-transitory computer-readable media of claim 19, wherein the second position of the end of the first robotic arm determines a third plane within the environment, and wherein the collision region is determined based on the first plane, the second plane, and the third plane.

21. The one or more non-transitory computer-readable media of claim 16, wherein the operations further comprise:

receiving, from an input device, input control data regarding movement of a medical instrument; and determining that the input control data is associated with movement of at least one of the first robotic arm or the second robotic arm into the collision region.

22. The one or more non-transitory computer-readable media of claim 16, wherein the first robotic arm is configured to operate in an admittance control mode in which user manipulation of the first robotic arm moves the first robotic arm, wherein determining that the end of the first robotic arm is in the first position is based on receiving user input, and wherein the user input is received responsive to the first robotic arm operating in the admittance control mode.

\* \* \* \* \*